(12) United States Patent
Overmyer et al.

(10) Patent No.: US 12,358,136 B2
(45) Date of Patent: Jul. 15, 2025

(54) GRASPING WORK DETERMINATION AND INDICATIONS THEREOF

(71) Applicant: Cilag GmbH International, Zug (CH)

(72) Inventors: Mark D. Overmyer, Cincinnati, OH (US); Raffaele J. DeFinis, Loveland, OH (US); David B. Smith, Mason, OH (US); Hamilton E. González, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 956 days.

(21) Appl. No.: 17/363,560

(22) Filed: Jun. 30, 2021

(65) Prior Publication Data
US 2023/0001579 A1 Jan. 5, 2023

(51) Int. Cl.
*B25J 9/16* (2006.01)
*A61B 34/30* (2016.01)

(52) U.S. Cl.
CPC ............ *B25J 9/1664* (2013.01); *A61B 34/30* (2016.02); *B25J 9/1633* (2013.01); *A61B 2562/0252* (2013.01)

(58) Field of Classification Search
CPC ......... A61B 34/30; A61B 34/35; A61B 34/76; A61B 34/70; A61B 34/37; A61B 34/20;
(Continued)

(56) References Cited

U.S. PATENT DOCUMENTS

| 2,366,274 A | 1/1945 | Luth et al. |
| 2,458,152 A | 1/1949 | Eakins |

(Continued)

FOREIGN PATENT DOCUMENTS

| CN | 201223445 Y | 4/2009 |
| CN | 102274074 A | 12/2011 |

(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Katherine H Schwiker
*Assistant Examiner* — Lauren Dubose

(57) ABSTRACT

A surgical system is disclosed. The surgical system comprises an end effector configured to move through a grasping motion, a motor configured to drive the grasping motion, an encoder configured to detect rotary positions, a load sensor configured to detect loads delivered, a position sensor configured to detect three-dimensional positions of the end effector, and a control circuit configured to receive a position parameter, a rotary parameter, and a load parameter, store the position parameter at the outset of the grasping motion, calculate an amount of work performed during the grasping motion while the position sensor detects the position of the end effector within a three-dimensional zone around the stored position parameter, transmit a work signal indicative of the amount of work performed, and reset the calculation of the amount of work performed when the position sensor detects a displacement of the end effector out of the three-dimensional zone.

7 Claims, 20 Drawing Sheets

(58) Field of Classification Search
CPC .............. A61B 34/74; A61B 2090/066; A61B 2090/067; A61B 2090/064; A61B 2090/031; A61B 2090/061; A61B 2090/0807; A61B 2090/065; A61B 2090/0811; A61B 17/29; A61B 17/28; A61B 2017/2932; A61B 2017/00022; A61B 2017/00017; A61B 2017/2926; A61B 2017/00398; A61B 2017/00119; A61B 2017/00199; A61B 90/06; A61B 2034/305; A61B 2034/2059; A61B 2034/301; A61B 2562/0252; A61B 18/1445; B25J 9/1628; B25J 9/1633; B25J 9/1656; B25J 9/1664; B25J 9/1666; B25J 9/1669; B25J 9/1679; B25J 9/1684; B25J 9/1694; B25J 13/085; B25J 13/088; B25J 13/089; B25J 13/082; B25J 15/00; B25J 9/1689; B25J 17/00; B25J 18/00; B25J 13/00; B25J 11/00; B25J 7/00; B25J 5/00; B25J 3/00; B25J 1/00; G06F 3/0346; G05D 1/0227; G05D 1/0274; G05B 2219/45083; G05B 2219/39505; Y10S 901/08; H02P 21/20; H02P 21/22; H02P 21/30; H02P 27/06; H02P 27/08; H02P 25/062; H02P 25/064; H02P 25/03
See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,633,874 A | 1/1987 | Chow et al. |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,910,389 A | 3/1990 | Sherman et al. |
| 4,920,978 A | 5/1990 | Colvin |
| 4,936,842 A | 6/1990 | D'Amelio et al. |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,004 A | 11/1993 | Bales et al. |
| 5,258,006 A | 11/1993 | Rydell et al. |
| 5,285,945 A | 2/1994 | Brinkerhoff et al. |
| 5,290,286 A | 3/1994 | Parins |
| 5,293,863 A | 3/1994 | Zhu et al. |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,339,723 A | 8/1994 | Huitema |
| 5,342,359 A | 8/1994 | Rydell |
| 5,361,583 A | 11/1994 | Huitema |
| 5,383,860 A | 1/1995 | Lau |
| 5,383,874 A | 1/1995 | Jackson et al. |
| 5,383,880 A | 1/1995 | Hooven |
| 5,383,888 A | 1/1995 | Zvenyatsky et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,524,643 A | 6/1996 | Faries, Jr. et al. |
| 5,529,235 A | 6/1996 | Boiarski et al. |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,611,813 A | 3/1997 | Lichtman |
| 5,618,307 A | 4/1997 | Donlon et al. |
| 5,624,452 A | 4/1997 | Yates |
| 5,647,871 A | 7/1997 | Levine et al. |
| 5,658,281 A | 8/1997 | Heard |
| 5,662,615 A | 9/1997 | Blake, III |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |

(56) References Cited

U.S. PATENT DOCUMENTS

| | | |
|---|---|---|
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,836,909 A | 11/1998 | Cosmescu |
| 5,836,943 A | 11/1998 | Miller, III |
| 5,853,412 A | 12/1998 | Mayenberger |
| 5,876,325 A | 3/1999 | Mizuno et al. |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,980,493 A | 11/1999 | Smith et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| 6,113,598 A | 9/2000 | Baker |
| H001904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,174,309 B1 | 1/2001 | Wrublewski et al. |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,241,724 B1 | 6/2001 | Fleischman et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,094 B1 | 5/2002 | Eitenmuller |
| 6,391,026 B1 | 5/2002 | Hung et al. |
| 6,398,779 B1 | 6/2002 | Buysse et al. |
| H002037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,458,130 B1 | 10/2002 | Frazier et al. |
| 6,461,363 B1 | 10/2002 | Gadberry et al. |
| 6,464,702 B2 | 10/2002 | Schulze et al. |
| 6,475,211 B2 | 11/2002 | Chess et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,290 B2 | 3/2003 | Adams et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,709,445 B2 | 3/2004 | Boebel et al. |
| 6,719,765 B2 | 4/2004 | Bonutti |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrodinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,134,587 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,208,005 B2 | 4/2007 | Frecker et al. |
| 7,220,951 B2 | 5/2007 | Truckai et al. |

(56) References Cited

U.S. PATENT DOCUMENTS

| | | |
|---|---|---|
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,451,904 B2 | 11/2008 | Shelton, IV |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,491,202 B2 | 2/2009 | Odom et al. |
| 7,494,501 B2 | 2/2009 | Ahlberg et al. |
| 7,498,080 B2 | 3/2009 | Tung et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,608,083 B2 | 10/2009 | Lee et al. |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,691,098 B2 | 4/2010 | Wallace et al. |
| 7,703,459 B2 | 4/2010 | Saadat et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,722,527 B2 | 5/2010 | Bouchier et al. |
| 7,722,607 B2 | 5/2010 | Dumbauld et al. |
| 7,727,244 B2 | 6/2010 | Orban, III et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter et al. |
| 7,841,980 B2 | 11/2010 | Minosawa et al. |
| 7,846,159 B2 | 12/2010 | Morrison et al. |
| 7,846,160 B2 | 12/2010 | Payne et al. |
| 7,850,688 B2 | 12/2010 | Hafner |
| 7,867,228 B2 | 1/2011 | Nobis et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,919,184 B2 | 4/2011 | Mohapatra et al. |
| 7,931,649 B2 | 4/2011 | Couture et al. |
| 7,935,114 B2 | 5/2011 | Takashino et al. |
| 7,935,130 B2 | 5/2011 | Williams |
| 7,955,322 B2 | 6/2011 | Devengenzo et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,980,443 B2 | 7/2011 | Scheib et al. |
| 7,981,113 B2 | 7/2011 | Truckai et al. |
| 7,982,776 B2 | 7/2011 | Dunki-Jacobs et al. |
| 7,995,045 B2 | 8/2011 | Dunki-Jacobs |
| 7,997,278 B2 | 8/2011 | Utley et al. |
| 8,016,855 B2 | 9/2011 | Whitman et al. |
| 8,020,743 B2 | 9/2011 | Shelton, IV |
| 8,048,070 B2 | 11/2011 | O'Brien et al. |
| 8,054,184 B2 | 11/2011 | Cline et al. |
| 8,058,771 B2 | 11/2011 | Giordano et al. |
| 8,066,167 B2 | 11/2011 | Measamer et al. |
| 8,070,036 B1 | 12/2011 | Knodel |
| 8,070,731 B2 | 12/2011 | Wenchell et al. |
| 8,075,555 B2 | 12/2011 | Truckai et al. |
| 8,075,558 B2 | 12/2011 | Truckai et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,128,624 B2 | 3/2012 | Couture et al. |
| 8,136,712 B2 | 3/2012 | Zingman |
| 8,141,762 B2 | 3/2012 | Bedi et al. |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,186,560 B2 | 5/2012 | Hess et al. |
| 8,187,267 B2 | 5/2012 | Pappone et al. |
| 8,197,446 B2 | 6/2012 | Beardsley |
| 8,197,472 B2 | 6/2012 | Lau et al. |
| 8,197,479 B2 | 6/2012 | Olson et al. |
| 8,210,411 B2 | 7/2012 | Yates et al. |
| 8,221,415 B2 | 7/2012 | Francischelli |
| 8,241,235 B2 | 8/2012 | Kahler et al. |
| 8,241,283 B2 | 8/2012 | Guerra et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |

(56) References Cited

U.S. PATENT DOCUMENTS

| | | |
|---|---|---|
| 8,277,447 B2 | 10/2012 | Garrison et al. |
| 8,277,471 B2 | 10/2012 | Wiener et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,232 B2 | 10/2012 | Unger |
| 8,303,583 B2 | 11/2012 | Hosier et al. |
| 8,308,040 B2 | 11/2012 | Huang et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,343,146 B2 | 1/2013 | Godara et al. |
| 8,343,171 B2 | 1/2013 | Farritor et al. |
| 8,348,126 B2 | 1/2013 | Olson et al. |
| 8,357,144 B2 | 1/2013 | Whitman et al. |
| 8,357,158 B2 | 1/2013 | McKenna et al. |
| 8,377,059 B2 | 2/2013 | Deville et al. |
| 8,388,646 B2 | 3/2013 | Chojin |
| 8,397,971 B2 | 3/2013 | Yates et al. |
| 8,403,926 B2 | 3/2013 | Nobis et al. |
| 8,414,577 B2 | 4/2013 | Boudreaux et al. |
| 8,423,182 B2 | 4/2013 | Robinson et al. |
| 8,425,410 B2 | 4/2013 | Murray et al. |
| 8,430,811 B2 | 4/2013 | Hess et al. |
| 8,430,876 B2 | 4/2013 | Kappus et al. |
| 8,453,906 B2 | 6/2013 | Huang et al. |
| 8,454,599 B2 | 6/2013 | Inagaki et al. |
| 8,460,288 B2 | 6/2013 | Tamai et al. |
| 8,460,292 B2 | 6/2013 | Truckai et al. |
| 8,484,833 B2 | 7/2013 | Cunningham et al. |
| 8,485,970 B2 | 7/2013 | Widenhouse et al. |
| 8,486,057 B2 | 7/2013 | Behnke, II |
| 8,491,533 B2 | 7/2013 | Parihar et al. |
| 8,491,625 B2 | 7/2013 | Horner |
| 8,496,682 B2 | 7/2013 | Guerra et al. |
| 8,512,364 B2 | 8/2013 | Kowalski et al. |
| 8,529,437 B2 | 9/2013 | Taylor et al. |
| 8,535,311 B2 | 9/2013 | Schall |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,579,176 B2 | 11/2013 | Smith et al. |
| 8,579,937 B2 | 11/2013 | Gresham |
| 8,591,459 B2 | 11/2013 | Clymer et al. |
| 8,591,506 B2 | 11/2013 | Wham et al. |
| 8,613,383 B2 | 12/2013 | Beckman et al. |
| 8,613,727 B2 | 12/2013 | Hart et al. |
| 8,616,431 B2 | 12/2013 | Timm et al. |
| 8,622,274 B2 | 1/2014 | Yates et al. |
| 8,623,016 B2 | 1/2014 | Fischer |
| 8,623,044 B2 | 1/2014 | Timm et al. |
| 8,628,529 B2 | 1/2014 | Aldridge et al. |
| 8,632,461 B2 | 1/2014 | Glossop |
| 8,636,736 B2 | 1/2014 | Yates et al. |
| 8,640,788 B2 | 2/2014 | Dachs, II et al. |
| 8,647,350 B2 | 2/2014 | Mohan et al. |
| 8,652,120 B2 | 2/2014 | Giordano et al. |
| 8,663,222 B2 | 3/2014 | Anderson et al. |
| 8,668,691 B2 | 3/2014 | Heard |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,784,418 B2 | 7/2014 | Romero |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,801,752 B2 | 8/2014 | Fortier et al. |
| 8,814,856 B2 | 8/2014 | Elmouelhi et al. |
| 8,827,995 B2 | 9/2014 | Schaller et al. |
| 8,828,023 B2 | 9/2014 | Neff et al. |
| 8,834,466 B2 | 9/2014 | Cummings et al. |
| 8,834,518 B2 | 9/2014 | Faller et al. |
| 8,851,354 B2 | 10/2014 | Swensgard et al. |
| 8,864,757 B2 | 10/2014 | Klimovitch et al. |
| 8,864,761 B2 | 10/2014 | Johnson et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,912,746 B2 | 12/2014 | Reid et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,961,515 B2 | 2/2015 | Twomey et al. |
| 8,979,843 B2 | 3/2015 | Timm et al. |
| 8,979,844 B2 | 3/2015 | White et al. |
| 8,986,302 B2 | 3/2015 | Aldridge et al. |
| 8,992,422 B2 | 3/2015 | Spivey et al. |
| 8,992,526 B2 | 3/2015 | Brodbeck et al. |
| 9,002,518 B2 | 4/2015 | Manzo et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,333 B2 | 4/2015 | Beale et al. |
| 9,028,494 B2 | 5/2015 | Shelton, IV et al. |
| 9,028,519 B2 | 5/2015 | Yates et al. |
| 9,039,695 B2 | 5/2015 | Giordano et al. |
| 9,039,705 B2 | 5/2015 | Takashino |
| 9,044,243 B2 | 6/2015 | Johnson et al. |
| 9,044,245 B2 | 6/2015 | Condie et al. |
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,072,535 B2 | 7/2015 | Shelton, IV et al. |
| 9,072,536 B2 | 7/2015 | Shelton, IV et al. |
| 9,089,360 B2 | 7/2015 | Messerly et al. |
| 9,095,362 B2 | 8/2015 | Dachs, II et al. |
| 9,101,385 B2 | 8/2015 | Shelton, IV et al. |
| 9,106,270 B2 | 8/2015 | Puterbaugh et al. |
| 9,107,684 B2 | 8/2015 | Ma |
| 9,113,900 B2 | 8/2015 | Buysse et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,149,324 B2 | 10/2015 | Huang et al. |
| 9,161,803 B2 | 10/2015 | Yates et al. |
| 9,168,054 B2 | 10/2015 | Turner et al. |
| 9,168,089 B2 | 10/2015 | Buysse et al. |
| 9,179,912 B2 | 11/2015 | Yates et al. |
| 9,192,431 B2 | 11/2015 | Woodruff et al. |
| 9,198,715 B2 | 12/2015 | Livneh |
| 9,204,879 B2 | 12/2015 | Shelton, IV |
| 9,220,559 B2 | 12/2015 | Worrell et al. |
| 9,226,751 B2 | 1/2016 | Shelton, IV et al. |
| 9,237,891 B2 | 1/2016 | Shelton, IV |

(56) References Cited

U.S. PATENT DOCUMENTS

| | | |
|---|---|---|
| 9,254,165 B2 | 2/2016 | Aronow et al. |
| 9,259,265 B2 | 2/2016 | Harris et al. |
| 9,259,277 B2 | 2/2016 | Rogers et al. |
| 9,265,567 B2 | 2/2016 | Orban, III et al. |
| 9,265,926 B2 | 2/2016 | Strobl et al. |
| 9,282,974 B2 | 3/2016 | Shelton, IV |
| 9,283,027 B2 | 3/2016 | Monson et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,320,563 B2 | 4/2016 | Brustad et al. |
| 9,333,025 B2 | 5/2016 | Monson et al. |
| 9,339,323 B2 | 5/2016 | Eder et al. |
| 9,339,342 B2 | 5/2016 | Prisco et al. |
| 9,345,481 B2 | 5/2016 | Hall et al. |
| 9,364,230 B2 | 6/2016 | Shelton, IV et al. |
| 9,375,232 B2 | 6/2016 | Hunt et al. |
| 9,386,983 B2 | 7/2016 | Swensgard et al. |
| 9,402,682 B2 | 8/2016 | Worrell et al. |
| 9,408,606 B2 | 8/2016 | Shelton, IV |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,864 B2 | 10/2016 | Witt et al. |
| 9,492,224 B2 | 11/2016 | Boudreaux et al. |
| 9,504,524 B2 | 11/2016 | Behnke, II |
| 9,526,407 B2 | 12/2016 | Hoeg et al. |
| 9,526,565 B2 | 12/2016 | Strobl |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,572,552 B1 | 2/2017 | Bodor et al. |
| 9,597,104 B2 | 3/2017 | Nicholas et al. |
| 9,597,143 B2 | 3/2017 | Madan et al. |
| 9,610,091 B2 | 4/2017 | Johnson et al. |
| 9,642,669 B2 | 5/2017 | Takashino et al. |
| 9,649,110 B2 | 5/2017 | Parihar et al. |
| 9,649,111 B2 | 5/2017 | Shelton, IV et al. |
| 9,668,806 B2 | 6/2017 | Unger et al. |
| 9,707,027 B2 | 7/2017 | Ruddenklau et al. |
| 9,737,355 B2 | 8/2017 | Yates et al. |
| 9,737,358 B2 | 8/2017 | Beckman et al. |
| 9,757,128 B2 | 9/2017 | Baber et al. |
| 9,757,186 B2 | 9/2017 | Boudreaux et al. |
| 9,763,661 B2 | 9/2017 | Zergiebel et al. |
| 9,782,214 B2 | 10/2017 | Houser et al. |
| 9,795,436 B2 | 10/2017 | Yates et al. |
| 9,808,308 B2 | 11/2017 | Faller et al. |
| 9,814,514 B2 | 11/2017 | Shelton, IV et al. |
| 9,820,740 B2 | 11/2017 | Zemlok et al. |
| 9,820,771 B2 | 11/2017 | Norton et al. |
| 9,861,428 B2 | 1/2018 | Trees et al. |
| 9,877,776 B2 | 1/2018 | Boudreaux |
| 9,888,942 B1 | 2/2018 | Savage et al. |
| 9,913,680 B2 | 3/2018 | Voegele et al. |
| 9,913,694 B2 | 3/2018 | Brisson |
| 9,937,626 B2 | 4/2018 | Rockrohr |
| 9,987,008 B2 | 6/2018 | Scirica et al. |
| 10,016,207 B2 | 7/2018 | Suzuki et al. |
| 10,070,916 B2 | 9/2018 | Artale |
| 10,092,310 B2 | 10/2018 | Boudreaux et al. |
| 10,098,527 B2 | 10/2018 | Weisenburgh, II et al. |
| 10,164,466 B2 | 12/2018 | Calderoni |
| 10,166,060 B2 | 1/2019 | Johnson et al. |
| 10,166,080 B2 | 1/2019 | Balicki et al. |
| 10,166,082 B1 | 1/2019 | Hariri et al. |
| 10,172,669 B2 | 1/2019 | Felder et al. |
| 10,172,687 B2 | 1/2019 | Garbus et al. |
| 10,179,413 B2 | 1/2019 | Rockrohr |
| 10,194,976 B2 | 2/2019 | Boudreaux |
| 10,213,266 B2 | 2/2019 | Zemlok et al. |
| 10,231,775 B2 | 3/2019 | Shelton, IV et al. |
| 10,251,672 B2 | 4/2019 | Meglan |
| 10,258,359 B2 | 4/2019 | Kapadia |
| 10,265,118 B2 | 4/2019 | Gerhardt |
| 10,278,721 B2 | 5/2019 | Dietz et al. |
| 10,321,964 B2 | 6/2019 | Grover et al. |
| 10,368,838 B2 | 8/2019 | Williams et al. |
| 10,376,338 B2 | 8/2019 | Taylor et al. |
| 10,390,895 B2 | 8/2019 | Henderson et al. |
| 10,398,517 B2 | 9/2019 | Eckert et al. |
| 10,420,620 B2 | 9/2019 | Rockrohr |
| 10,426,516 B2 | 10/2019 | Racenet et al. |
| 10,463,421 B2 | 11/2019 | Boudreaux et al. |
| 10,470,830 B2 | 11/2019 | Hill et al. |
| 10,507,068 B2 | 12/2019 | Kopp et al. |
| 10,517,686 B2 | 12/2019 | Vokrot et al. |
| 10,537,351 B2 | 1/2020 | Shelton, IV et al. |
| 10,548,504 B2 | 2/2020 | Shelton, IV et al. |
| 10,561,470 B2 | 2/2020 | Hourtash et al. |
| 10,588,706 B2 | 3/2020 | Limon |
| 10,624,691 B2 | 4/2020 | Wiener et al. |
| 10,639,111 B2 | 5/2020 | Kopp |
| 10,653,489 B2 | 5/2020 | Kopp |
| 10,667,877 B2 | 6/2020 | Kapadia |
| 10,675,104 B2 | 6/2020 | Kapadia |
| 10,716,639 B2 | 7/2020 | Kapadia et al. |
| 10,736,219 B2 | 8/2020 | Seow et al. |
| 10,743,872 B2 | 8/2020 | Leimbach et al. |
| 10,751,087 B2 | 8/2020 | Morgan et al. |
| 10,765,484 B2 | 9/2020 | Bonutti et al. |
| 10,772,688 B2 | 9/2020 | Peine et al. |
| 10,779,849 B2 | 9/2020 | Shelton, IV et al. |
| 10,779,897 B2 | 9/2020 | Rockrohr |
| 10,779,900 B2 | 9/2020 | Pedros et al. |
| 10,799,304 B2 | 10/2020 | Kapadia et al. |
| 10,806,454 B2 | 10/2020 | Kopp |
| 10,813,703 B2 | 10/2020 | Swayze et al. |
| 10,849,700 B2 | 12/2020 | Kopp et al. |
| 10,881,399 B2 | 1/2021 | Shelton, IV et al. |
| 10,893,884 B2 | 1/2021 | Stoddard et al. |
| 10,898,280 B2 | 1/2021 | Kopp |
| 10,912,616 B2 | 2/2021 | Dachs, II et al. |
| 10,932,772 B2 | 3/2021 | Shelton, IV et al. |
| 10,959,788 B2 | 3/2021 | Grover et al. |
| 10,980,610 B2 | 4/2021 | Rosenberg et al. |
| 11,013,569 B2 | 5/2021 | Shelton, IV et al. |
| 11,026,764 B2 | 6/2021 | Kopp |
| 11,045,265 B2 | 6/2021 | Seow et al. |
| 11,058,504 B2 | 7/2021 | Blanco et al. |
| 11,090,125 B2 | 8/2021 | Peine et al. |
| 11,109,866 B2 | 9/2021 | Shelton, IV et al. |
| 11,160,623 B2 | 11/2021 | Hagn |
| 11,207,146 B2 | 12/2021 | Shelton, IV et al. |
| 11,229,471 B2 | 1/2022 | Shelton, IV et al. |
| 11,278,362 B2 | 3/2022 | Shelton, IV et al. |
| 11,298,128 B2 | 4/2022 | Messerly et al. |
| 11,304,699 B2 | 4/2022 | Shelton, IV et al. |
| 11,364,067 B2 | 6/2022 | Murrell et al. |
| 11,369,443 B2 | 6/2022 | Shelton, IV et al. |
| 11,376,082 B2 | 7/2022 | Shelton, IV et al. |
| 11,376,083 B2 | 7/2022 | Harris et al. |
| 11,382,704 B2 | 7/2022 | Overmyer et al. |
| 11,389,164 B2 | 7/2022 | Yates et al. |
| 11,399,906 B2 | 8/2022 | Shelton, IV et al. |
| 11,413,102 B2 | 8/2022 | Shelton, IV et al. |
| 11,432,885 B2 | 9/2022 | Shelton, IV et al. |
| 11,478,312 B2 | 10/2022 | Klingbeil et al. |
| 11,510,747 B2 | 11/2022 | Zemlok et al. |
| 11,523,859 B2 | 12/2022 | Shelton, IV et al. |
| 11,547,465 B2 | 1/2023 | Shelton, IV et al. |
| 11,547,468 B2 | 1/2023 | Shelton, IV et al. |
| 11,559,307 B2 | 1/2023 | Shelton, IV et al. |
| 11,559,308 B2 | 1/2023 | Yates et al. |
| 11,576,677 B2 | 2/2023 | Shelton, IV et al. |
| 11,589,888 B2 | 2/2023 | Shelton, IV et al. |
| 11,607,239 B2 | 3/2023 | Swensgard et al. |
| 11,607,278 B2 | 3/2023 | Shelton, IV et al. |
| 11,612,445 B2 | 3/2023 | Shelton, IV et al. |
| 11,659,023 B2 | 5/2023 | Shelton, IV et al. |
| 11,696,760 B2 | 7/2023 | Shelton, IV et al. |
| 11,723,729 B2 | 8/2023 | Shelton, IV et al. |
| 2002/0022836 A1 | 2/2002 | Goble et al. |

(56) References Cited

U.S. PATENT DOCUMENTS

| | | |
|---|---|---|
| 2002/0072736 A1 | 6/2002 | Tierney et al. |
| 2003/0014053 A1 | 1/2003 | Nguyen et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0229344 A1 | 12/2003 | Dycus et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0249374 A1 | 12/2004 | Tetzlaff et al. |
| 2004/0260273 A1 | 12/2004 | Wan |
| 2005/0006432 A1 | 1/2005 | Racenet et al. |
| 2005/0015125 A1 | 1/2005 | Mioduski et al. |
| 2005/0033278 A1 | 2/2005 | McClurken et al. |
| 2005/0090817 A1 | 4/2005 | Phan |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0267464 A1 | 12/2005 | Truckai et al. |
| 2006/0064086 A1 | 3/2006 | Odom |
| 2006/0069306 A1 | 3/2006 | Banik et al. |
| 2006/0135978 A1 | 6/2006 | Franer |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0032704 A1 | 2/2007 | Gandini et al. |
| 2007/0073185 A1 | 3/2007 | Nakao |
| 2007/0073341 A1 | 3/2007 | Smith et al. |
| 2007/0078395 A1 | 4/2007 | Valaie |
| 2007/0135826 A1 | 6/2007 | Zaver et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0260242 A1 | 11/2007 | Dycus et al. |
| 2007/0265613 A1 | 11/2007 | Edelstein et al. |
| 2007/0282358 A1 | 12/2007 | Remiszewski et al. |
| 2008/0015575 A1 | 1/2008 | Odom et al. |
| 2008/0064921 A1 | 3/2008 | Larkin et al. |
| 2008/0071269 A1 | 3/2008 | Hilario et al. |
| 2008/0081948 A1 | 4/2008 | Weisenburgh et al. |
| 2008/0114355 A1 | 5/2008 | Whayne et al. |
| 2008/0125794 A1 | 5/2008 | Brock et al. |
| 2008/0147058 A1 | 6/2008 | Horrell et al. |
| 2008/0147062 A1 | 6/2008 | Truckai et al. |
| 2008/0188755 A1 | 8/2008 | Hart |
| 2008/0281315 A1 | 11/2008 | Gines |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0182327 A1 | 7/2009 | Unger |
| 2009/0182332 A1 | 7/2009 | Long et al. |
| 2009/0248021 A1 | 10/2009 | McKenna |
| 2009/0248037 A1 | 10/2009 | Prisco |
| 2009/0248041 A1 | 10/2009 | Williams et al. |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0168520 A1 | 7/2010 | Poll et al. |
| 2010/0222752 A1 | 9/2010 | Collins, Jr. et al. |
| 2010/0228264 A1 | 9/2010 | Robinson et al. |
| 2010/0274278 A1 | 10/2010 | Fleenor et al. |
| 2011/0028964 A1 | 2/2011 | Edwards |
| 2011/0230719 A1 | 9/2011 | Katakura et al. |
| 2011/0290856 A1 | 12/2011 | Shelton, IV et al. |
| 2011/0295295 A1 | 12/2011 | Shelton, IV et al. |
| 2011/0301414 A1 | 12/2011 | Hotto et al. |
| 2011/0306840 A1 | 12/2011 | Allen et al. |
| 2011/0306967 A1 | 12/2011 | Payne et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078244 A1 | 3/2012 | Worrell et al. |
| 2012/0109186 A1 | 5/2012 | Parrott et al. |
| 2012/0111920 A1 | 5/2012 | Kostrzewski |
| 2012/0116222 A1 | 5/2012 | Sawada et al. |
| 2012/0116265 A1 | 5/2012 | Houser et al. |
| 2012/0132018 A1 | 5/2012 | Tang et al. |
| 2012/0238827 A1 | 9/2012 | Berry et al. |
| 2012/0303025 A1 | 11/2012 | Garrison |
| 2013/0023915 A1 | 1/2013 | Mueller |
| 2013/0023925 A1 | 1/2013 | Mueller |
| 2013/0085510 A1 | 4/2013 | Stefanchik et al. |
| 2013/0123776 A1 | 5/2013 | Monson et al. |
| 2013/0331730 A1 | 12/2013 | Fenech et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0066944 A1 | 3/2014 | Taylor et al. |
| 2014/0207135 A1 | 7/2014 | Winter |
| 2014/0246477 A1 | 9/2014 | Koch, Jr. et al. |
| 2014/0263552 A1 | 9/2014 | Hall et al. |
| 2014/0276944 A1 | 9/2014 | Farritor et al. |
| 2014/0343569 A1 | 11/2014 | Turner |
| 2014/0371763 A1 | 12/2014 | Poll et al. |
| 2015/0038981 A1 | 2/2015 | Kilroy et al. |
| 2015/0080876 A1 | 3/2015 | Worrell et al. |
| 2015/0114404 A1 | 4/2015 | Czop et al. |
| 2015/0272659 A1 | 10/2015 | Boudreaux et al. |
| 2016/0015261 A1 | 1/2016 | Kishi et al. |
| 2016/0051316 A1 | 2/2016 | Boudreaux |
| 2016/0113728 A1 | 4/2016 | Piron et al. |
| 2016/0175028 A1 | 6/2016 | Trees et al. |
| 2016/0346930 A1 | 12/2016 | Hares |
| 2016/0361122 A1 | 12/2016 | Seeber |
| 2016/0361127 A1 | 12/2016 | Dachs, II et al. |
| 2017/0028562 A1 | 2/2017 | Yamazaki et al. |
| 2017/0079708 A1 | 3/2017 | Gilbert et al. |
| 2017/0079730 A1 | 3/2017 | Azizian et al. |
| 2017/0105785 A1 | 4/2017 | Shelton, IV et al. |
| 2017/0135771 A1 | 5/2017 | Auld et al. |
| 2017/0188802 A1 | 7/2017 | Lawrence et al. |
| 2017/0224428 A1 | 8/2017 | Kopp |
| 2017/0333145 A1 | 11/2017 | Griffiths et al. |
| 2018/0085175 A1 | 3/2018 | Steinle et al. |
| 2018/0192862 A1 | 7/2018 | Ide |
| 2018/0289427 A1 | 10/2018 | Griffiths et al. |
| 2018/0296286 A1 | 10/2018 | Peine et al. |
| 2019/0053866 A1 | 2/2019 | Seow et al. |
| 2019/0059986 A1 | 2/2019 | Shelton, IV et al. |
| 2019/0083182 A1 | 3/2019 | Roach et al. |
| 2019/0094084 A1 | 3/2019 | Swinehart et al. |
| 2019/0104919 A1 | 4/2019 | Shelton, IV et al. |
| 2019/0125457 A1 | 5/2019 | Parihar et al. |
| 2019/0133703 A1 | 5/2019 | Seow et al. |
| 2019/0167267 A1 | 6/2019 | Kobayashi et al. |
| 2019/0183596 A1 | 6/2019 | Dachs |
| 2019/0200844 A1 | 7/2019 | Shelton, IV et al. |
| 2019/0200981 A1 | 7/2019 | Harris et al. |
| 2019/0201045 A1 | 7/2019 | Yates et al. |
| 2019/0201111 A1 | 7/2019 | Shelton, IV et al. |
| 2019/0201135 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0298471 A1 | 10/2019 | Holop |
| 2019/0314107 A1 | 10/2019 | Worrell et al. |
| 2019/0321112 A1 | 10/2019 | Cecil |
| 2019/0328469 A1 | 10/2019 | Ando et al. |
| 2019/0357884 A1 | 11/2019 | Williams et al. |
| 2020/0000536 A1 | 1/2020 | Yakimovich et al. |
| 2020/0054412 A1 | 2/2020 | Fuerst et al. |

(56) References Cited

U.S. PATENT DOCUMENTS

| | | |
|---|---|---|
| 2020/0078109 A1 | 3/2020 | Steger et al. |
| 2020/0093554 A1 | 3/2020 | Schuh et al. |
| 2020/0197108 A1 | 6/2020 | Usui |
| 2020/0214776 A1 | 7/2020 | Hingwe et al. |
| 2020/0246063 A1 | 8/2020 | Shelton, IV et al. |
| 2020/0281675 A1 | 9/2020 | Meglan |
| 2020/0315715 A1 | 10/2020 | Rockrohr et al. |
| 2020/0315721 A1 | 10/2020 | Rabindran et al. |
| 2020/0405401 A1 | 12/2020 | Shelton, IV et al. |
| 2020/0405415 A1 | 12/2020 | Shelton, IV et al. |
| 2020/0405421 A1 | 12/2020 | Luck |
| 2021/0015519 A1 | 1/2021 | Meglan et al. |
| 2021/0059777 A1 | 3/2021 | Overmyer et al. |
| 2021/0068889 A1 | 3/2021 | Shelton, IV et al. |
| 2021/0093409 A1* | 4/2021 | Overmyer .............. A61B 34/76 |
| 2021/0196356 A1 | 7/2021 | Shelton, IV et al. |
| 2021/0212777 A1 | 7/2021 | Cheng |
| 2021/0346109 A1* | 11/2021 | Hares ...................... A61B 5/24 |
| 2021/0401524 A1 | 12/2021 | Suresh et al. |
| 2022/0031350 A1 | 2/2022 | Witte |
| 2022/0054208 A1 | 2/2022 | Cooper et al. |
| 2022/0202437 A1 | 6/2022 | Overmyer et al. |
| 2022/0202514 A1 | 6/2022 | Boudreaux |
| 2022/0202517 A1 | 6/2022 | Overmyer et al. |
| 2022/0203519 A1 | 6/2022 | Overmyer et al. |
| 2022/0218407 A1 | 7/2022 | Shelton, IV et al. |
| 2022/0287782 A1 | 9/2022 | Shelton, IV et al. |
| 2023/0000491 A1 | 1/2023 | Wise et al. |
| 2023/0000542 A1 | 1/2023 | Murrell |
| 2023/0000578 A1 | 1/2023 | Moubarak |
| 2023/0320776 A1 | 10/2023 | Shelton, IV et al. |

FOREIGN PATENT DOCUMENTS

| | | |
|---|---|---|
| DE | 29623113 U1 | 10/1997 |
| DE | 20004812 U1 | 9/2000 |
| DE | 10201569 A1 | 7/2003 |
| EP | 0705571 A1 | 4/1996 |
| EP | 2060238 A1 | 5/2009 |
| EP | 1747761 B1 | 10/2009 |
| JP | H08229050 A | 9/1996 |
| SU | 578972 A1 | 11/1977 |
| WO | WO-8103272 A1 | 11/1981 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-2004078051 A2 | 9/2004 |
| WO | WO-2010104755 A1 | 9/2010 |
| WO | WO-2012044606 A2 | 4/2012 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Heat-induced changes in the mechanics of a collagenous tissue: pseudoelastic behavior at 37° C.," Journal of Biomechanics, 31, pp. 211-216 (1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Covidien Brochure, [Value Analysis Brief], LigaSure Advance™ Pistol Grip, dated Rev. Apr. 2010 (7 pages).

Covidien Brochure, LigaSure Atlas™ Hand Switching Instruments, dated Dec. 2008 (2 pages).

Covidien Brochure, LigaSure Impact™ Instrument LF4318, dated Feb. 2013 (3 pages).

Covidien Brochure, The LigaSure Precise™ Instrument, dated Mar. 2011 (2 pages).

Covidien Brochure, The LigaSure™ 5 mm Blunt Tip Sealer/Divider Family, dated Apr. 2013 (2 pages).

Douglas, S.C. "Introduction to Adaptive Filter". Digital Signal Processing Handbook. Ed. Vijay K. Madisetti and Douglas B. Williams. Boca Raton: CRC Press LLC, 1999.

Erbe Electrosurgery VIO® 200 S, (2012), p. 7, 12 pages, accessed Mar. 31, 2014 at http://www.erbe-med.com/erbe/media/Marketing materialien/85140170 ERBE En Vio 200 S D027541.

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Glaser and Subak-Sharpe, Integrated Circuit Engineering, Addison-Wesley Publishing, Reading, MA (1979). (book—not attached).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Henriques. F.C., "Studies in thermal injury V. The predictability and the significance of thermally induced rate processes leading to irreversible epidermal injury." Archives of Pathology, 434, pp. 489-502 (1947).

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

Humphrey, J.D., "Continuum Thermomechanics and the Clinical Treatment of Disease and Injury," Appl. Mech. Rev., vol. 56, No. 2 pp. 231-260 (Mar. 2003).

IEEE Std 802.3-2012 (Revision of IEEE Std 802.3-2008, published Dec. 28, 2012.

International Preliminary Report on Patentability, Application No. PCT/US2013/046777, dated Dec. 31, 2014 (5 pages).

International Search Report, Application No. PCT/US2013/046777, dated Oct. 1, 2013 (4 pages).

Jang, J. et al. "Neuro-fuzzy and Soft Computing." Prentice Hall, 1997, pp. 13-89, 199-293, 335- 393, 453-496, 535-549.

Kurt Gieck & Reiner Gieck, Engineering Formulas § Z.7 (7th ed. 1997).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

National Semiconductors Temperature Sensor Handbook—http://www.national.com/appinfo/tempsensors/files/temphb.pdf; accessed online: Apr. 1, 2011.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

Wall et al., "Thermal modification of collagen," J Shoulder Elbow Surg, No. 8, pp. 339-344 (Jul./Aug. 1999).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(56) References Cited

OTHER PUBLICATIONS

Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb. 1998. ASME Journal of Biomechanical Engineering, vol. 120, pp. 22-26.
International Preliminary Report on Patentability for Application No. PCT/IB2022/055928, dated Dec. 14, 2023 (15 pages).
International Search Report and Written Opinion for Application No. PCT/IB2022/055928, dated Nov. 21, 2022 (23 pages).

* cited by examiner

GRASPING WORK DETERMINATION AND INDICATIONS THEREOF

BACKGROUND

The present disclosure relates to surgical systems, surgical devices, and surgical techniques. Surgical devices include motor-driven and/or robotic surgical devices configured to grasp tissue.

SUMMARY

In one general aspect, the present disclosure provides a surgical system, comprising an end effector. The end effector comprises a first jaw and a second jaw, wherein at least one of the first jaw and the second jaw is configured to move through a grasping motion to grasp tissue therebetween. The surgical system further comprises a motor configured to drive the grasping motion, an encoder configured to detect rotary positions of the motor, and a load sensor configured to detect loads delivered by the motor. The surgical system further comprises a position sensor configured to detect three-dimensional positions of the end effector, and a control circuit comprising a processor and a memory communicatively coupled to the processor. The memory stores program instructions executable by the processor to receive a position parameter from the position sensor, a rotary parameter from the encoder, and a load parameter from the load sensor. The memory further stores program instructions executable by the processor to store the position parameter at the outset of the grasping motion in the memory, and calculate an amount of work performed by the motor during the grasping motion from the rotary parameter and the load parameter while the position sensor detects the position of the end effector remaining within a three-dimensional zone around the position parameter stored at the outset of the grasping motion. The memory further stores program instructions executable by the processor to transmit a work signal to a communication device indicative of the amount of work performed by the motor during the grasping motion, and reset the calculation of the amount of work performed by the motor during the grasping motion when the position sensor detects a displacement of the end effector out of the three-dimensional zone around the position parameter stored at the outset of the grasping motion.

In another aspect, the present disclosure provides a surgical system, comprising an end effector comprising a first jaw and a second jaw, wherein at least one of the first jaw and the second jaw is configured to move through a grasping motion to grasp tissue therebetween. The surgical system further comprises a motor configured to drive the grasping motion, a rotary encoder configured to detect rotary positions of the motor, a torque sensor configured to detect torques delivered by the motor, and a control circuit comprising a processor and a memory communicatively coupled to the processor. The memory stores a nominal torque threshold and program instructions executable by the processor to receive rotary parameters from the rotary encoder and torque parameters from the torque sensor, accumulate an amount of work performed by the motor during the grasping motion from the rotary parameters and the torque parameters excluding work performed when the torque parameter is less than the nominal torque threshold, and transmit a work signal to a communication device indicative of the accumulated amount of work.

In another aspect, the present disclosure provides a surgical system, comprising an end effector comprising a first jaw and a second jaw, wherein at least one of the first jaw and the second jaw is configured to move through a grasping motion to grasp tissue therebetween. The surgical system further comprises a first motor and a second motor configured to drive the grasping motion, a first rotary encoder configured to detect rotary positions of the first motor, and a second rotary encoder configured to detect rotary positions of the second motor. The surgical system further comprises a first torque sensor configured to detect torques delivered by the first motor, a second torque sensor configured to detect torques delivered by the second motor, and a control circuit comprising a processor and a memory communicatively coupled to the processor. The memory stores a nominal torque threshold and program instructions executable by the processor to receive rotary parameters from the first rotary encoder and the second rotary encoder, receive torque parameters from the first torque sensor and the second torque sensor, and calculate an average torque from the torque parameters. The memory further stores program instructions executable by the processor to accumulate an amount of work performed by the motor during the grasping motion from the rotary parameters and the torque parameters excluding work performed when the average torque is less than the nominal torque threshold, and transmit a work signal to a communication device indicative of the accumulated amount of work.

In yet another aspect, the present disclosure provides a surgical system, comprising an end effector comprising a first jaw and a second jaw, wherein at least one of the first jaw and the second jaw is configured to move through a grasping motion to grasp tissue therebetween. The surgical system further comprises a motor configured to drive the grasping motion, a rotary encoder configured to detect rotary positions of the motor, and a torque sensor configured to detect torques delivered by the motor. The surgical system further comprises a control circuit comprising a processor and a memory communicatively coupled to the processor, wherein the memory stores a tissue metric lookup table in which a tissue metric output is associated with a maximum grasp angle. The memory further stores program instructions executable by the processor to receive rotary parameters from the rotary encoder and torque parameters from the torque sensor, calculate the work performed by the motor from the rotary parameters and the torque parameters, and identify the tissue metric output associated with the maximum grasp angle. The maximum grasp angle corresponds to the maximum rotary position of the motor during the grasping motion. The memory further stores program instructions executable by the processor to normalize the work performed by the motor based on the tissue metric output, and transmit a tissue metric signal to a communication device indicative of the work normalized with the tissue metric output.

BRIEF DESCRIPTION OF THE FIGURES

The novel features of the various aspects are set forth with particularity in the appended claims. The described aspects, however, both as to organization and methods of operation, may be best understood by reference to the following description, taken in conjunction with the accompanying drawings in which:

Corresponding reference characters indicate corresponding parts throughout the several views. The exemplifications set out herein illustrate various aspects of the present disclosure, in one form, and such exemplifications are not to be construed as limiting the scope of the invention in any manner.

DETAILED DESCRIPTION

Figure 1:
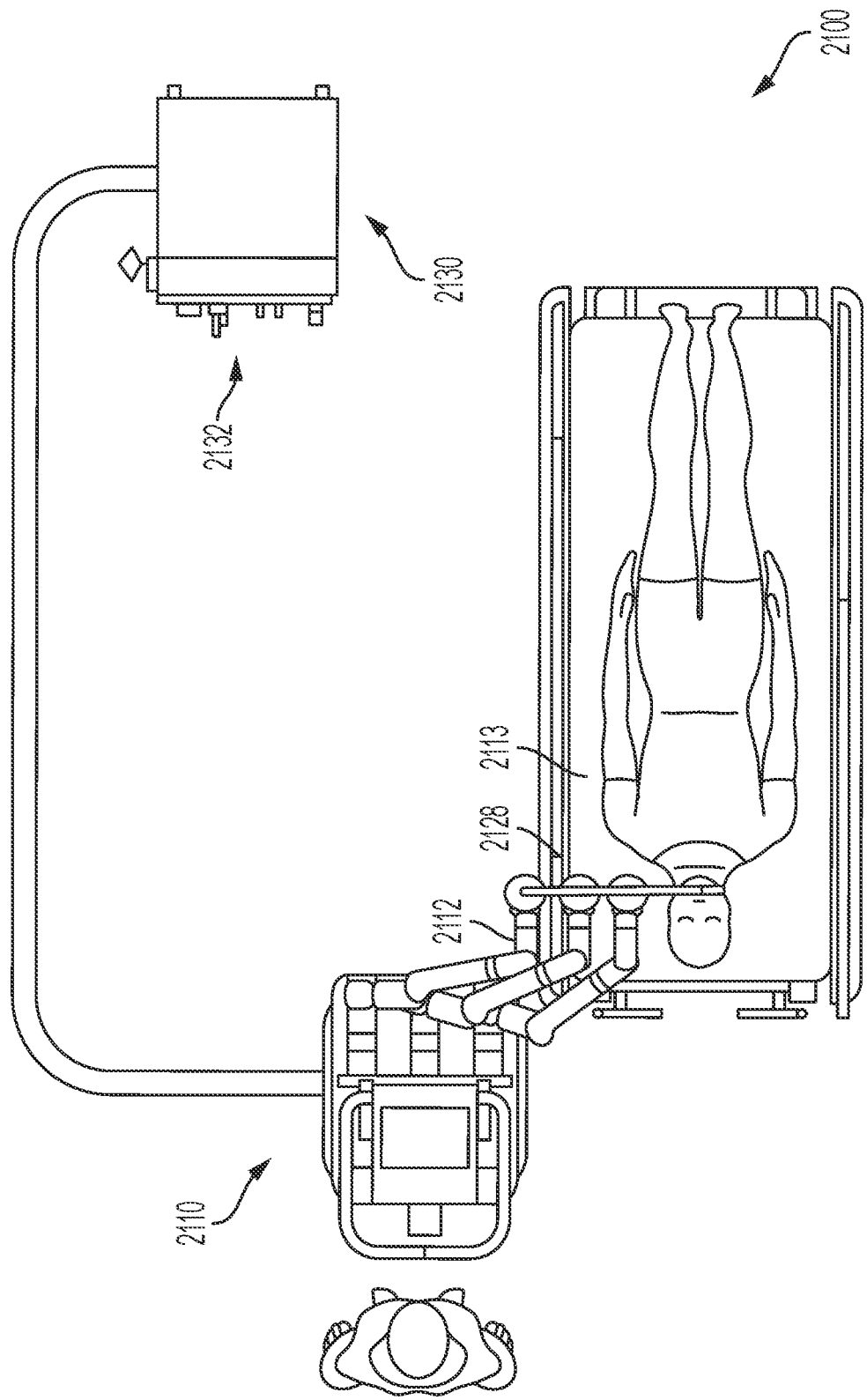
FIG. 1 is a plan view of a surgical procedure depicting a cart-based robotic system arranged for diagnostic and/or therapeutic bronchoscopy procedure(s), in accordance with at least one aspect of the present disclosure.

Applicant of the present application also owns the following U.S. patent applications, filed on Jun. 30, 2021, each of which is herein incorporated by reference in its entirety:

U.S. patent application Ser. No. 17/363,565, titled STAPLE CARTRIDGE REPLACEMENT, now U.S. Pat. No. 11,931,026;

U.S. patent application Ser. No. 17/363,573, titled LINK-DRIVEN ARTICULATION DEVICE FOR A SURGICAL DEVICE, now U.S. Pat. No. 11,974,829; and U.S. patent application Ser. No. 17/363,578, titled ELECTROSURGICAL TOOL WITH CAPACITIVE COUPLING MITIGATION SHEATH ASSEMBLY, now U.S. Patent Application Publication No. 2023/0000542.

Applicant of the present application also owns the following U.S. patent applications, filed Dec. 30, 2020, each of which is herein incorporated by reference in its entirety:

U.S. patent application Ser. No. 17/137,829, titled SURGICAL TOOL WITH TOOL-BASED TRANSLATION AND LOCK FOR THE SAME;

U.S. patent application Ser. No. 17/137,846, titled ROBOTIC SURGICAL TOOLS HAVING DUAL ARTICULATION DRIVES;

U.S. patent application Ser. No. 17/137,852, titled TORQUE-BASED TRANSITION BETWEEN OPERATING GEARS; and U.S. patent application Ser. No. 17/137,857, titled DUAL DRIVING PINION CROSSCHECK.

Applicant of the present application also owns U.S. patent application Ser. No. 16/587,744, filed Sep. 30, 2019, titled COMMUNICATING CLOSURE EFFORT FOR ROBOTIC SURGICAL TOOLS BACKGROUND, which published Apr. 1, 2021 as U.S. Patent Application Publication No. 2021/0093409, which is incorporated by reference herein in its entirety.

Applicant of the present application also owns U.S. patent application Ser. No. 16/553,725, filed Aug. 28, 2019, titled ARTICULATING INCLUDING ANTAGONISTIC CONTROLS FOR ARTICULATION AND CALIBRATION, which published Mar. 4, 2021 as U.S. Patent Application Publication No. 2021/0059777, which is incorporated by reference herein in its entirety.

Applicant of the present application also owns the following U.S. patent applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS, which issued May 25, 2021 as U.S. Pat. No. 11,013,563;

U.S. patent application Ser. No. 15/940,676, titled AUTOMATIC TOOL ADJUSTMENTS FOR ROBOT-ASSISTED SURGICAL PLATFORMS, which published Jul. 4, 2019 as U.S. Patent Application Publication No. 2019/0201142; and U.S. patent application Ser. No. 15/940,711, titled SENSING ARRANGEMENTS FOR ROBOT-ASSISTED SURGICAL PLATFORMS, which published Jul. 4, 2019 as U.S. Patent Application Publication No. 2019/0201120.

Applicant of the present application also owns U.S. Provisional Patent Application Ser. No. 62/611,339, titled ROBOT ASSISTED SURGICAL PLATFORM, filed Dec. 28, 2017, which is incorporated by reference herein in its entirety.

Application of the present application also owns U.S. patent application Ser. No. 13/118,241, titled SURGICAL STAPLING INSTRUMENTS WITH ROTATABLE STAPLE DEPLOYMENT ARRANGEMENTS, filed May 27, 2011, which issued Jul. 7, 2015 as U.S. Pat. No. 9,072,535, which is incorporated by reference herein in its entirety.

U.S. Pat. No. 10,470,830, titled SYSTEM AND METHODS FOR INSTRUMENT BASED INSERTION ARCHITECTURES, issued Nov. 12, 2019, is also incorporated by reference herein in its entirety.

Before explaining various aspects of a robotic surgical platforms and surgical devices in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Minimally-invasive surgery (MIS), such as laparoscopic surgery and bronchoscopy, typically involves techniques intended to reduce tissue damage during a surgical procedure. For example, laparoscopic procedures can involve creating a number of small incisions in the patient (e.g., in the abdomen) and introducing one or more surgical tools (e.g., end effectors and an endoscope) through the incisions into the patient. Bronchoscopy can involve passing a bronchoscope through a patient's nose and/or mouth, down the patient's throat, and into the patient's lungs. Surgical procedures may then be performed using the introduced surgical tools and with visualization aid provided by the endoscope, for example.

MIS may provide certain benefits, such as reduced patient scarring, less patient pain, shorter patient recovery periods, and/or lower medical treatment costs associated with patient recovery. Recent technological developments allow robotic systems to perform more MIS procedures. The robotic systems typically include one or more robotic arms for manipulating surgical tools based on commands from a remote operator (e.g. surgeon/clinician). A robotic arm may, for example, support at its distal end various surgical devices such as surgical end effectors, imaging devices, and cannulas for providing access to the patient's body cavity and organs.

Existing robotically-assisted surgical systems typically consist of a surgeon console and a patient-side cart with one or more interactive robotic arms controlled from the console. For example, one robotic arm can support a camera and the other robotic arm(s) can support robotic tools such as scalpels, scissors, graspers, and staplers, for example. Various exemplary robotic tools are further described herein.

A robotic surgical system disclosed herein can be a software-controlled, electro-mechanical system designed for clinicians to perform MIS procedures. The robotic surgical system can be used with an endoscope, compatible endoscopic instruments, and accessories. The system may be used by trained clinicians (e.g. physicians/surgeons) in an operating room environment to assist in the accurate control of compatible endoscopic instruments during robotically-assisted urologic, gynecologic, gastrological, and other laparoscopic surgical procedures. The compatible endoscopic instruments and accessories for use with the surgical system are intended for endoscopic manipulation of tissue including stapling, grasping, cutting, blunt and sharp dissection, approximation, ligation, electrocautery, and suturing, for example.

An exemplary robotic system 2100 is shown in FIG. 1, which depicts a cart-based robotically-enabled system arranged for a diagnostic and/or therapeutic bronchoscopy procedure. During a bronchoscopy, the system 2100 may include a cart 2110 having one or more robotic arms 2112 to deliver a surgical device, such as a steerable endoscope 2113, which may be a procedure-specific bronchoscope for bronchoscopy, to a natural orifice access point (i.e., the mouth of the patient positioned on a table in the present example) to deliver diagnostic and/or therapeutic tools. As shown, the cart 2110 may be positioned proximate to the patient's upper torso in order to provide access to the access point. Similarly, the robotic arms 2112 may be actuated to position the bronchoscope relative to the access point. The arrangement in FIG. 1 may also be utilized when performing a gastro-intestinal (GI) procedure with a gastroscope, a specialized endoscope for GI procedures.

With continued reference to FIG. 1, once the cart 2110 is properly positioned, the robotic arms 2112 may insert the steerable endoscope 2113 into the patient robotically, manually, or a combination thereof. The endoscope 2113 may be directed down the patient's trachea and lungs after insertion using precise commands from the robotic system until reaching the target destination or operative site. For example, the endoscope 2113 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 2113 may endoscopically deliver tools to resect the potentially cancerous tissue. In some instances, diagnostic and therapeutic treatments can be delivered in separate procedures. In those circumstances, the endoscope 2113 may also be used to deliver a fiducial to "mark" the location of the target nodule as well. In other instances, diagnostic and therapeutic treatments may be delivered during the same procedure.

The system 2100 may also include a movable tower 2130, which may be connected via support cables to the cart 2110 to provide support for controls, electronics, fluidics, optics, sensors, and/or power to the cart 2110. Placing such functionality in the tower 2130 allows for a smaller form factor cart 2110 that may be more easily adjusted and/or repositioned by an operating clinician (e.g. surgeon) and his/her staff. Additionally, the division of functionality between the cart/table and the tower 2130 reduces operating room clutter and facilitates improving clinical workflow. While the cart 2110 may be positioned close to the patient, the tower 2130 may be stowed in a remote location to stay out of the way during a procedure.

In support of the robotic systems described above, the tower 2130 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 2130 or the cart 2110, may control the entire system or sub-system(s) thereof. For example, when executed by a processor of the computer system, the instructions may cause the components of the robotics system to actuate the relevant carriages and arm mounts, actuate the robotics arms, and control the robotic surgical tools. For example, in response to receiving the control signal, the motors in the joints of the robotics arms may position the arms into a certain posture.

The tower 2130 may also include a pump, flow meter, valve control, and/or fluid access in order to provide controlled irrigation and aspiration capabilities to the system that may be deployed through the endoscope 2113. These components may also be controlled using the computer system of tower 2130. In some aspects, irrigation and aspiration capabilities may be delivered directly to the endoscope 2113 through separate cable(s).

The tower 2130 may include a voltage and surge protector designed to provide filtered and protected electrical power to the cart 2110, thereby avoiding placement of a power transformer and other auxiliary power components in the cart 2110, resulting in a smaller, more moveable cart 2110.

The tower 2130 may also include support equipment for the sensors deployed throughout the robotic system 2100. For example, the tower 2130 may include opto-electronics equipment for detecting, receiving, and processing data received from the optical sensors or cameras throughout the robotic system 2100. In combination with the control system, such opto-electronics equipment may be used to generate real-time images for display in any number of consoles deployed throughout the system, including in the tower 2130. Similarly, the tower 2130 may also include an electronic subsystem for receiving and processing signals received from deployed electromagnetic (EM) sensors. The tower 2130 may also be used to house and position an EM field generator for detection by EM sensors in or on the robotic surgical tool. The tower 2130 can also house an electrosurgical generator for supplying RF current to a robotic surgical tool, such as monopolar scissors, for example.

The tower 2130 may also include a console 2132 in addition to other consoles available in the rest of the system, e.g., a console mounted on top of the cart 2110. The console 2132 may include a user interface and a display screen, such as a touchscreen, for the clinician. Consoles in the system 2100 are generally designed to provide both robotic controls as well as pre-operative and real-time information of the procedure, such as navigational and localization information of the endoscope 2113. When the console 2132 is not the only console available to the clinician, it may be used by a second clinician, such as a nurse, for example, to monitor the health or vitals of the patient and the operation of system, as well as provide procedure-specific data, such as navigational and localization information. In other aspects, the console 2132 is housed in a body that is separate from the tower 2130.

The tower 2130 may be coupled to the cart 2110 and endoscope 2113 through one or more cables or connections. In some aspects, the support functionality from the tower 2130 may be provided through a single cable to the cart 2110, simplifying and de-cluttering the operating room. In other aspects, specific functionality may be coupled in separate cabling and connections. For example, while power may be provided through a single power cable to the cart, the support for controls, optics, fluidics, and/or navigation may be provided through one or more separate cables.

Figure 2:
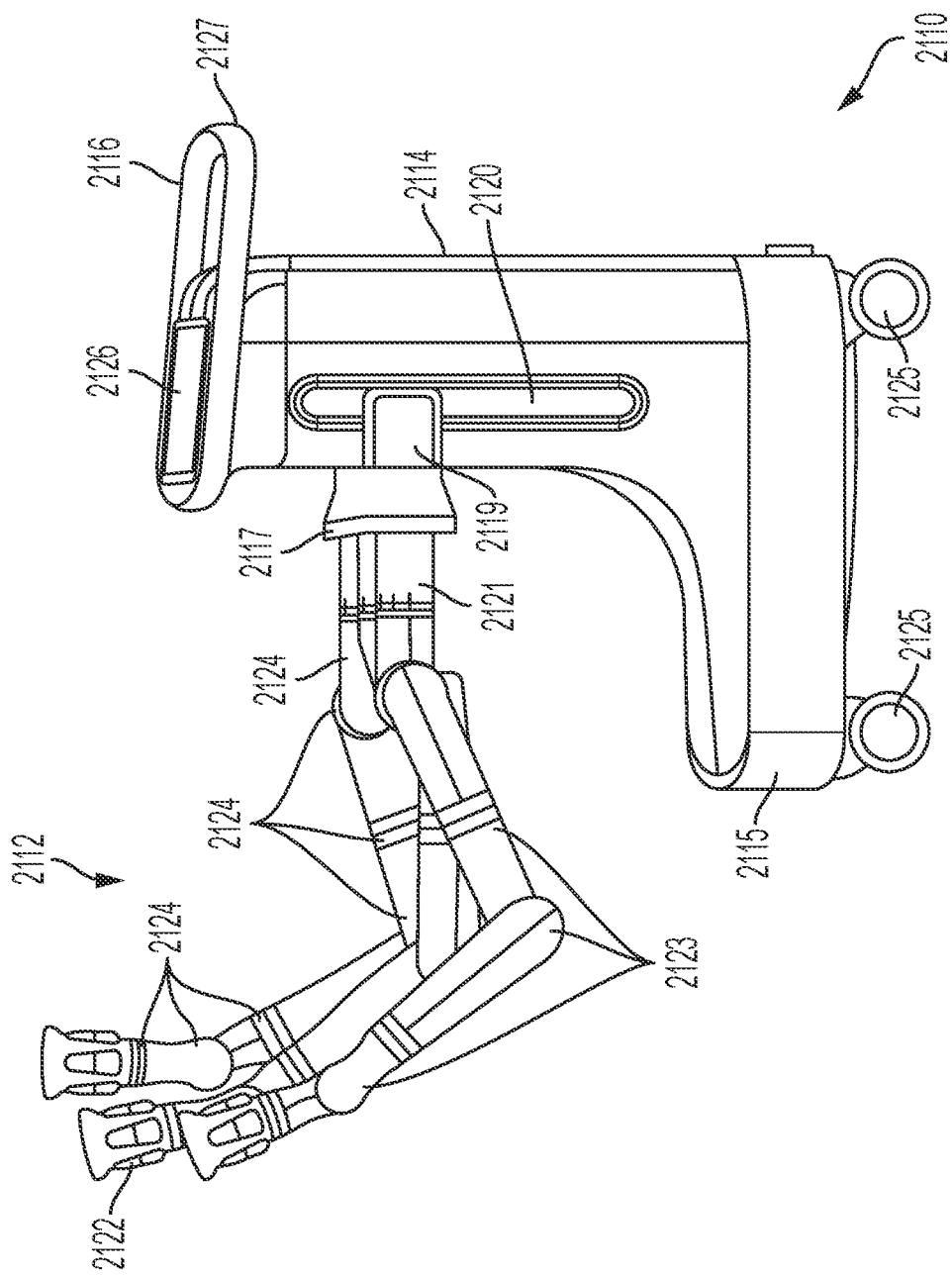
FIG. 2 is a perspective view of a robotic arm cart of the cart-based robotic system of FIG. 1, in accordance with at least one aspect of the present disclosure.

FIG. 2 depicts the cart 2110 from the cart-based robotically-enabled system 2100 shown in FIG. 1. The cart 2110 generally includes an elongated support structure 2114 (often referred to as a "column"), a cart base 2115, and a console 2116 at the top of the elongated support structure 2114. The elongated support structure 2114 may include one or more carriages, such as a carriage 2117 (alternatively "arm support") for supporting the deployment of one or more robotic arms 2112 (three shown in FIG. 2). The carriage 2117 may include individually configurable arm mounts that rotate along a perpendicular axis to adjust the base of the robotic arms 2112 for better positioning relative to the patient. The carriage 2117 also includes a carriage interface 2119 that allows the carriage 2117 to vertically translate along the elongated support structure 2114.

The carriage interface 2119 is connected to the elongated support structure 2114 through slots, such as slot 2120, that are positioned on opposite sides of the elongated support structure 2114 to guide the vertical translation of the carriage 2117. The slot 2120 contains a vertical translation interface to position and hold the carriage at various vertical heights relative to the cart base 2115. Vertical translation of the carriage 2117 allows the cart 2110 to adjust the reach of the robotic arms 2112 to meet a variety of table heights, patient sizes, and physician preferences. Similarly, the individually configurable arm mounts on the carriage 2117 allow the robotic arm base 2121 of robotic arms 2112 to be angled in a variety of configurations.

The elongated support structure 2114 may include internal mechanisms, such as gears and motors, that are designed to use a vertically aligned lead screw to translate the carriage 2117 in a mechanized fashion in response to control signals generated in response to user inputs, e.g., inputs from the console 2116.

The robotic arms 2112 may generally include robotic arm bases 2121 and tool drivers 2122, separated by a series of linkages 2123 that are connected by a series of joints 2124, each joint including an independent actuator, each actuator including an independently controllable motor. Each independently controllable joint represents an independent degree of freedom available to the robotic arm. Each of the arms 2112 have seven joints, and thus provide seven degrees of freedom. A multitude of joints result in a multitude of degrees of freedom, allowing for "redundant" degrees of freedom. Redundant degrees of freedom allow the robotic arms 2112 to position their respective tool drivers 2122 at a specific position, orientation, and trajectory in space using different linkage positions and joint angles. This allows for the system to position and direct a robotic surgical tool from a desired point in space while allowing the clinician to move the arm joints into a clinically advantageous position away from the patient to create greater access while avoiding arm collisions.

The cart base 2115 balances the weight of the elongated support structure 2114, carriage 2117, and arms 2112 over the floor. Accordingly, the cart base 2115 houses heavier components, such as electronics, motors, power supply, as well as components that either enable movement and/or immobilize the cart. For example, the cart base 2115 includes rollable wheel-shaped casters 2125 that allow for the cart 2110 to easily move around the room prior to a procedure. After reaching the appropriate position, the casters 2125 may be immobilized using wheel locks to hold the cart 2110 in place during the procedure.

Positioned at a vertical end of elongated support structure 2114, the console 2116 allows for both a user interface for receiving user input and a display screen (or a dual-purpose device such as, for example, a touchscreen 2126) to provide the clinician with both pre-operative and intra-operative data. Potential pre-operative data on the touchscreen 2126 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 2116 may be positioned and tilted to allow a clinician to access the console from the side of the elongated support structure 2114 opposite carriage 2117. From this position, the clinician may view the console 2116, robotic arms 2112, and patient while operating the console 2116 from behind the cart 2110. As shown, the console 2116 also includes a handle 2127 to assist with maneuvering and stabilizing cart 2110.

The distal end of the system's robotic arms include the tool driver 2122 (alternatively referred to as "instrument drive mechanism" or "instrument device manipulator" (IDM)) that incorporate electro-mechanical means for actuating the robotic tool. A removable or detachable robotic tool can be releasably mounted to the tool driver 2122. The robotic tool can be devoid of any electro-mechanical components, such as motors. This dichotomy may be driven by the need to sterilize robotic surgical tools used in medical procedures, and the inability to adequately sterilize expensive capital equipment due to their intricate mechanical assemblies and sensitive electronics. Accordingly, the robotic surgical tools may be designed to be detached, removed, and interchanged from the instrument driver (and thus the system) for individual sterilization or disposal by the clinician or the clinician's staff. In contrast, the instrument drivers need not be changed or sterilized, and may be draped for protection.

Figure 3:
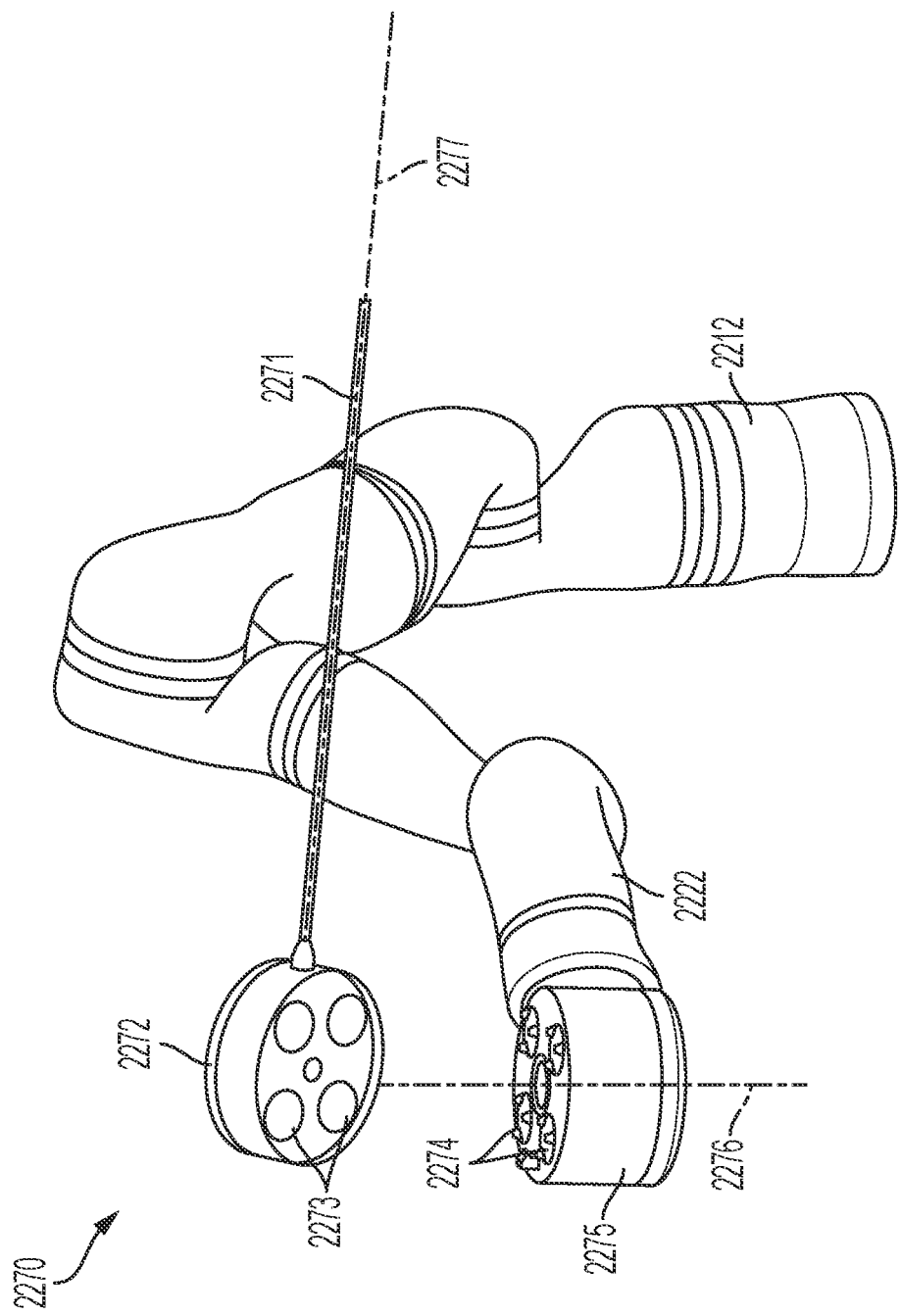
FIG. 3 is a perspective view of a robotic arm having a tool driver and a paired robotic tool detached from the tool driver, in accordance with at least one aspect of the present disclosure.
Figure 4:
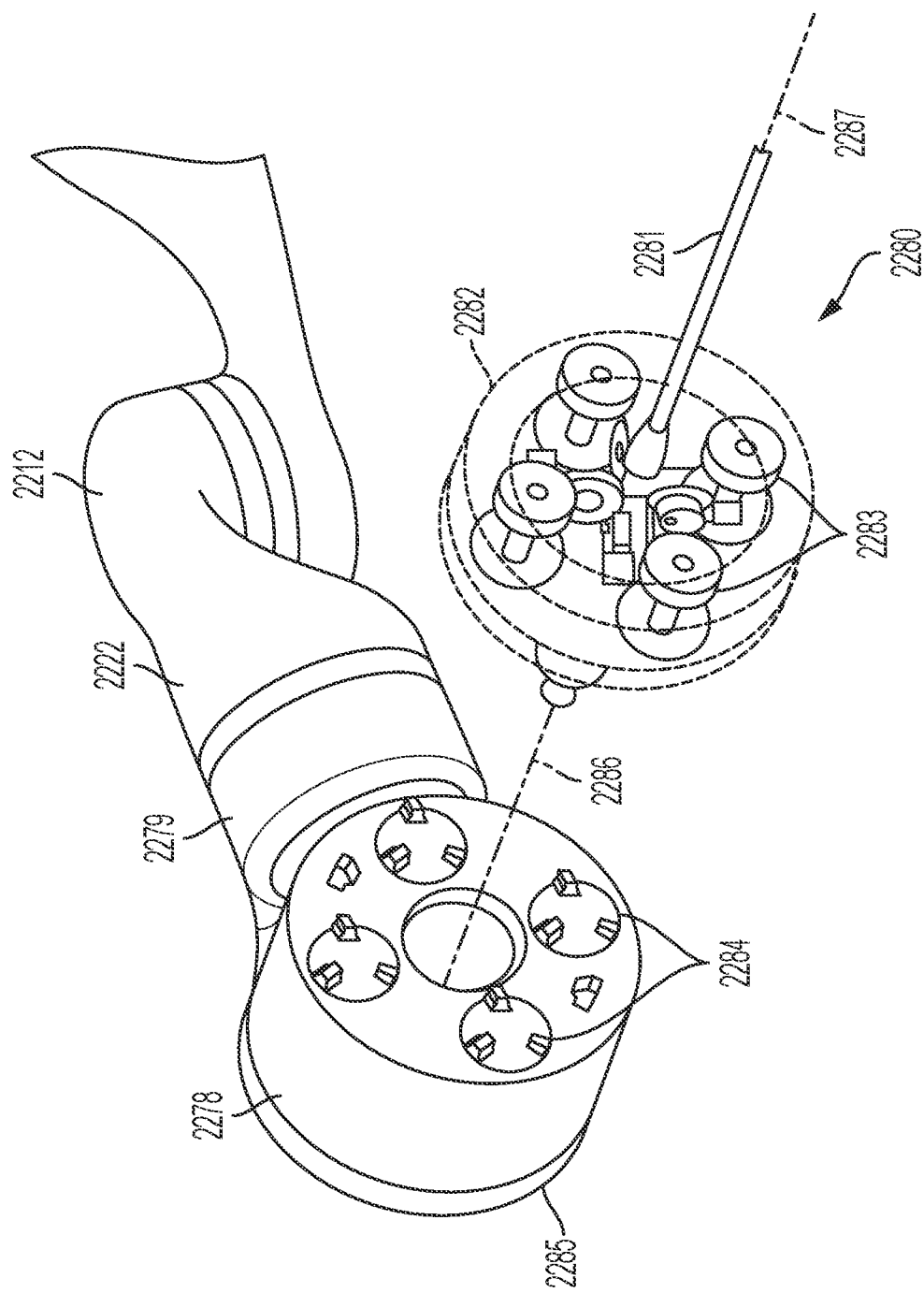
FIG. 4 is another perspective view of the robotic arm of FIG. 3 having a tool driver and a paired robotic tool detached from the tool driver, in accordance with at least one aspect of the present disclosure.

FIGS. 3 and 4 illustrate an example tool driver paired with a robotic surgical tool. The tool drivers are positioned at the distal end 2222 of a robotic arm 2212, which can be similar in many aspects to the robotic arms 2112. Positioned at the distal end 2222 of the robotic arm 2212, the tool drivers comprises one or more drive units arranged with parallel axes to provide controlled torque to a robotic surgical tool via drive shafts. Each drive unit includes an individual drive shaft for interacting with the instrument, a gear head for converting the motor shaft rotation to a desired torque, a motor for generating the drive torque, an encoder to measure the speed of the motor shaft and provide feedback to the control circuitry, and control circuity for receiving control signals and actuating the drive unit. Each drive unit being independently controlled and motorized, the tool driver may provide multiple (four as shown in FIGS. 3 and 4) independent drive outputs to the robotic surgical tool. In operation, the control circuitry can receive a control signal, transmit a motor signal to the motor, compare the resulting motor speed as measured by the encoder with the desired speed, and modulate the motor signal to generate the desired torque, for example.

For procedures that require a sterile environment, the robotic system may incorporate a drive interface, such as a sterile adapter connected to a sterile drape, that sits between the tool driver and the robotic surgical tool. The chief purpose of the sterile adapter is to transfer angular motion from the drive shafts of the tool driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the tool driver and drive inputs on the instrument. Connected to the sterile adapter, the sterile drape, comprised of a thin, flexible material such as transparent or translucent plastic, is designed to cover the capital equipment, such as the tool driver, the robotic arm, and the cart (in a cart-based system) or table (in a table-based system). Use of the drape would allow the capital equipment to be positioned proximate to the patient while still being located in an area not requiring sterilization (i.e., non-sterile field). On the other side of the sterile drape, the robotic surgical tool may interface with the patient in an area requiring sterilization (i.e., sterile field).

Robotic surgical platforms like the robotic surgical system 2100 are further described in U.S. Patent Application Publication No. 2021/0059777, titled ARTICULATING INCLUDING ANTAGONISTIC CONTROLS FOR ARTICULATION AND CALIBRATION, published Mar. 4, 2021. U.S. Patent Application Publication No. 2021/0059777, titled ARTICULATING INCLUDING ANTAGONISTIC CONTROLS FOR ARTICULATION AND CALIBRATION, published Mar. 4, 2021 is incorporated by reference herein in its entirety.

FIG. 3 depicts a robotic surgical tool 2270 with a paired tool driver 2275. The tool driver 2275 can be coupled to a distal end 2222 of the robotic arm 2212. Like other surgical tools designed for use with a robotic system, the robotic surgical tool 2270 includes an elongated shaft 2271 (or elongate body) and a housing (or base) 2272. The housing 2272, can also be referred to as an "instrument handle" due to its intended design for manual interaction by the clinician when attaching or coupling the surgical tool 2270 to the tool driver 2275 on the robotic arm 2212. The housing 2272 includes rotatable drive inputs 2273, e.g., receptacles, pulleys or spools, that are designed to be mated with drive outputs 2274 that extend through a drive interface on tool driver 2275 at the distal end 2222 of the robotic arm 2212. When physically connected, latched, and/or coupled, the mated drive inputs 2273 of housing 2272 may share axes of rotation with the drive outputs 2274 in the tool driver 2275 to allow the transfer of torque from drive outputs 2274 to drive inputs 2273. In some instances, the drive outputs 2274 may include splines that are designed to mate with receptacles on the drive inputs 2273. The drive outputs 2274 (and drive inputs 2273 when drivingly coupled thereto) are configured to rotate about axes parallel with a central axis 2276 defined through the tool driver 2275.

The elongated shaft 2271 is designed to be delivered through either an anatomical opening or lumen, e.g., as in endoscopy, or a minimally invasive incision, e.g., as in laparoscopy. The elongated shaft 2271 may be either flexible (e.g., having properties similar to an endoscope) or rigid (e.g., having properties similar to a laparoscope) or contain a customized combination of both flexible and rigid portions. In an unflexed configuration, the elongated shaft 2271 extends along a longitudinal axis 2277, which is transverse to the central axis 2276 of the tool driver 2275. When designed for laparoscopy, the distal end of a rigid elongated shaft may be connected to an end effector extending from a jointed wrist formed from a clevis with at least one degree of freedom and a surgical tool or robotic surgical tool, such as, for example, a grasper, scissors, a stapler, or other surgical device. The end effector can be actuated based on force from the tendons as the drive inputs 2273 rotate in response to torque received from the drive outputs 2274 of the tool driver 2275. Various highly articulatable robotic surgical tools are further described herein. When designed for endoscopy, the distal end of a flexible elongated shaft may include a steerable or controllable bending section that may be articulated and bent based on torque received from the drive outputs 2274 of the tool driver 2275.

Torque from the tool driver 2275 is transmitted down the elongated shaft 2271 using tendons along the shaft 2271. These individual tendons, such as pull wires, may be individually anchored to individual drive inputs 2273 within the housing 2272. From the housing 2272, the tendons are directed down one or more pull lumens along the elongated shaft 2271 and anchored at the distal portion of the elongated shaft 2271 or in the wrist at the distal portion of the elongated shaft 2271. During a surgical procedure, such as a laparoscopic, endoscopic or hybrid procedure, these tendons may be coupled to a distally mounted end effector, such as a grasper or scissors, for example. Under such an arrangement, torque exerted on drive inputs 2273 would transfer tension to the tendon, thereby causing the end effector to actuate in some way. In some instances, during a surgical procedure, the tendon may cause a joint to rotate about an axis, thereby causing the end effector to move in one direction or another. Alternatively, the tendon may be connected to one or more jaws of a grasper at distal end of the elongated shaft 2271, where tension from the tendon cause the grasper to close.

In endoscopy, the tendons may be coupled to a bending or articulating section positioned along the elongated shaft 2271 (e.g., at the distal end) via adhesive, a control ring, or other mechanical fixation. When fixedly attached to the distal end of a bending section, torque exerted on drive inputs 2273 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 2271 to allow for controlled articulation in the desired bending or articulable sections.

In endoscopy, the elongated shaft 2271 houses a number of components to assist with the robotic procedure. The shaft may include a working channel for deploying surgical tools (or robotic surgical tools), irrigation, and/or aspiration to the operative region at the distal end of the shaft 2271. The shaft 2271 may also accommodate wires and/or optical fibers to transfer signals to/from an optical assembly at the distal tip, which may include an optical camera. The shaft 2271 may also accommodate optical fibers to carry light from proximally-located light sources, such as light emitting diodes, to the distal end of the shaft. In various instances, an RF electrode can extend through the elongated shaft 2271 and can be configured to deliver RF energy to a distal end effector of the robotic surgical tool 2270.

At the distal end of the robotic surgical tool 2270, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

Referring still to FIG. 3, the drive shaft axes, and thus the drive input axes, are parallel to the central axis 2276 of the tool driver 2275 and orthogonal to the longitudinal axis 2277 of the elongated shaft. This arrangement, however, can complicate roll capabilities for the elongated shaft 2271 in certain instances. Rolling the elongated shaft 2271 along its longitudinal axis 2277 while keeping the drive inputs 2273 static may result in undesirable tangling of the tendons as they extend off the drive inputs 2273 and enter pull lumens within the elongated shaft 2271. The resulting entanglement of such tendons may disrupt any control algorithms intended to predict movement of the flexible elongated shaft during an endoscopic procedure.

FIG. 4 illustrates another tool driver 2285 and a paired robotic surgical tool 2280 where the axes of the drive units are parallel to an axis defined by an elongated shaft 2281 of the surgical tool 2280. As shown, a circular tool driver 2285 comprises four drive units with their drive outputs 2284 aligned in parallel at the end of the robotic arm 2212. The drive units, and their respective drive outputs 2284, are housed in a rotational assembly 2278 of the tool driver 2285 that is driven by one of the drive units within the rotational assembly 2278. In response to torque provided by the rotational drive unit, the rotational assembly 2278 rotates along a circular bearing that connects the rotational assembly 2278 to a non-rotational portion 2279 of the tool driver 2285. Power and controls signals may be communicated from the non-rotational portion 2279 of the tool driver 2285 to the rotational assembly 2278 through electrical contacts, which can be maintained through rotation by a brushed slip ring connection. In other aspects of the present disclosure, the rotational assembly 2278 may be responsive to a separate drive unit that is integrated into the non-rotational portion 2279, and thus not in parallel to the other drive units. The rotational assembly 2278 allows the tool driver 2285 to rotate the drive units, and their respective drive outputs 2284, as a single unit around a tool driver axis 2286.

Similar to the robotic surgical tool 2270, the robotic surgical tool 2280 includes an elongated shaft portion 2281 and a housing 2282 (shown as transparent in FIG. 4 for illustrative purposes) including a plurality of drive inputs 2283 (such as receptacles, pulleys, and spools) that are configured to receive the drive outputs 2284 in the tool driver 2285. Shaft 2281 extends from the center of the housing 2282 along a longitudinal axis 2287 substantially parallel to the axes of the drive inputs 2283, rather than orthogonal thereto as in the arrangement shown in FIG. 3.

When coupled to the rotational assembly 2278 of the tool driver 2285, the robotic surgical tool 2280, comprising the housing 2282 and shaft 2281, rotates in combination with the rotational assembly 2278 about a central axis 2286 defined through the tool driver 2285. Since the shaft 2281 is positioned at the center of the housing 2282, the shaft 2281 is coaxial with tool driver's central axis 2286 when attached. Thus, rotation of the rotational assembly 2278 causes the shaft 2281 to rotate about its own longitudinal axis 2287. Moreover, as the rotational assembly 2278 rotates with the shaft 2281, any tendons connected to the drive inputs 2283 in the housing 2282 are not tangled during rotation. Accordingly, the parallelism of the axes of the drive outputs 2284, drive inputs 2283, and shaft 2281 allows for the shaft rotation without tangling any control tendons.

In other instances, the tool drives may include a different configuration of actuated drives. For example, U.S. Patent Application Publication No. 2019/0201111, titled DRIVE ARRANGEMENTS FOR ROBOTIC-ASSISTED SURGICAL PLATFORMS, which published on Jul. 4, 2019, describes tool carriages having various drive arrangements. U.S. Pat. No. 9,072,535, titled SURGICAL STAPLING INSTRUMENTS WITH ROTATABLE STAPLE DEPLOYMENT ARRANGEMENTS, which issued Jul. 7, 2015, also describes tool carriages having various drive arrangements. U.S. Pat. No. 9,072,535, titled SURGICAL STAPLING INSTRUMENTS WITH ROTATABLE STAPLE DEPLOYMENT ARRANGEMENTS, which issued Jul. 7, 2015, and U.S. Patent Application Publication No. 2019/0201111, titled DRIVE ARRANGEMENTS FOR ROBOTIC-ASSISTED SURGICAL PLATFORMS, which published on Jul. 4, 2019, are incorporated by reference herein in their respective entireties. Alternative drive arrangements are further described herein.

Figure 5:
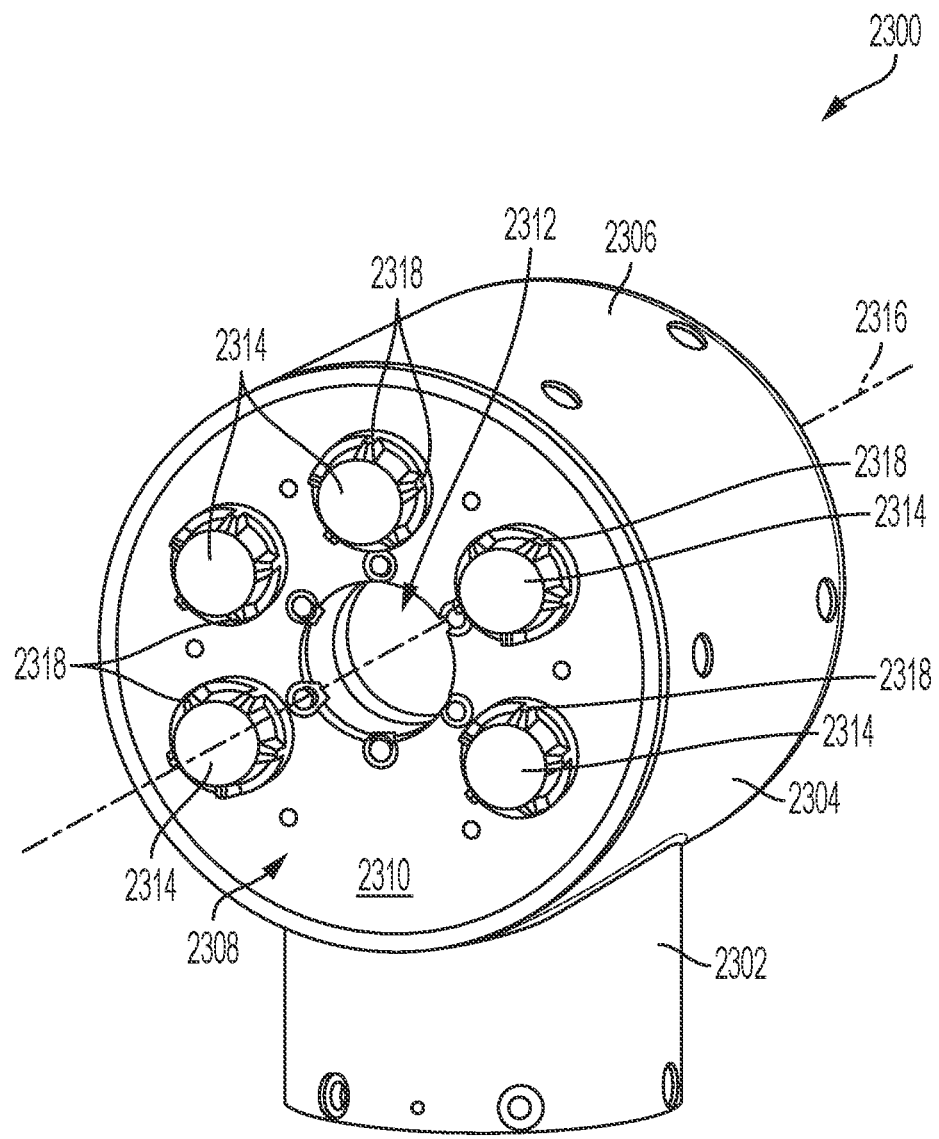
FIG. 5 is a perspective view of a tool driver, in accordance with at least one aspect of the present disclosure.

FIG. 5 depicts a perspective view of another tool driver 2300, which is also referred to herein as an IDM. The tool driver 2300 is similar in many aspects to the tool drivers 2285; however, the tool driver 2300 includes five rotary outputs. Various aspects of the tool driver 2300 are further described in U.S. Pat. No. 10,470,830, titled SYSTEM AND METHODS FOR INSTRUMENT BASED INSERTION ARCHITECTURES, issued Nov. 12, 2019, for example.

The tool driver 2300 can be used with the robotic surgical system 2100 and with the robotic arms 2212, for example. The tool driver 2300 is configured to attach a surgical tool to a robotic arm in a manner that allows the surgical tool to be continuously rotated, or "rolled", about a longitudinal axis of the surgical tool. The tool driver 2300 includes a base 2302 and a surgical tool holder assembly 2304 coupled to the base 2302. The surgical tool holder assembly 2304 serves as a tool holder for holding a robotic surgical tool.

Figure 6:
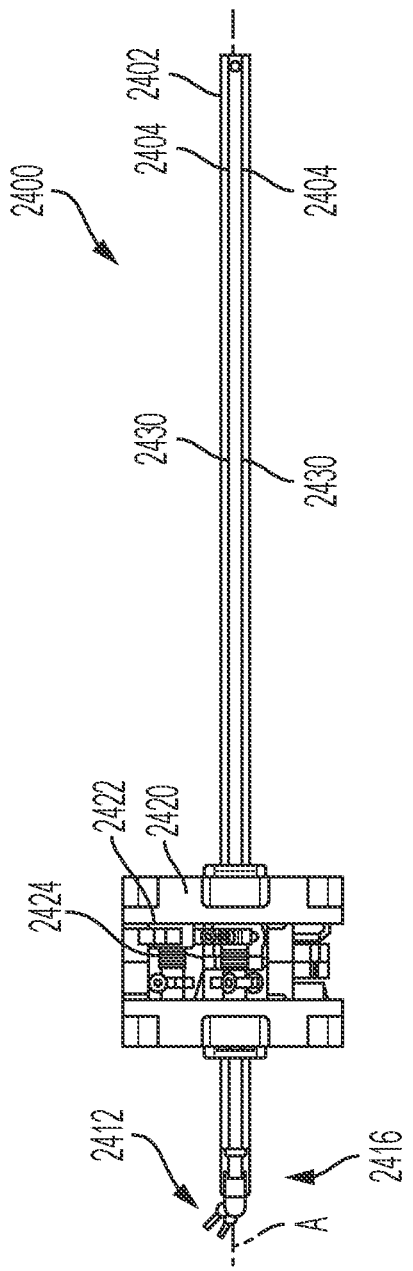
FIG. 6 is an elevation view of a surgical tool for use with the tool driver of FIG. 5, in accordance with at least one aspect of the present disclosure.

The surgical tool holder assembly 2304 further includes an outer housing 2306, a surgical tool holder 2308, an attachment interface 2310, a passage 2312, and a plurality of torque couplers 2314 that have splines 2318. The passage 2312 comprises a through-bore that extends from one face of the tool driver 2300 to an opposing face of the tool driver 2300 along a central axis 2316, which is collinear with a longitudinal axis of the surgical tool coupled thereto. The tool driver 2300 can be used with a variety of surgical tools, which may include a handle, or housing, and an elongated body, or shaft, and which may be for a laparoscope, an endoscope, or other types of surgical tools, such as electrosurgical tools including monopolar RF scissors, for example. An exemplary surgical tool 2400 is shown in FIG. 6, for example.

The base 2302 removably or fixedly mounts the tool driver 2300 to a robotic surgical arm of a robotic surgical system. In FIG. 5, the base 2302 is fixedly attached to the outer housing 2306 of the surgical tool holder assembly 2304. In alternative instances, the base 2302 is structured to include a platform, which is adapted to rotatably receive the surgical tool holder 2308 on the face opposite from the attachment interface 2310. The platform may include a passage aligned with the passage 2312 to receive the elongated body of the surgical tool and, in some instances, an additional elongated body of a second surgical tool mounted coaxially with the first surgical tool. One or more motors can be housed in the base 2302. For example, the surgical tool holder 2308 can include multiple motors, which are configured to drive, i.e. rotate output drives, also referred to herein as torque drivers and torque couplers, 2314 with a torque and rotary velocity, which can be controlled by the controller, for example.

The surgical tool holder assembly 2304 is configured to secure a surgical tool to the tool driver 2300 and rotate the surgical tool relative to the base 2302. Mechanical and electrical connections are provided from the surgical arm to the base 2302 and then to the surgical tool holder assembly 2304 to rotate the surgical tool holder 2308 relative to the outer housing 2306 and to manipulate and/or deliver power and/or signals from the surgical arm to the surgical tool holder 2308 and ultimately to the surgical tool. Signals may include signals for pneumatic pressure, electrical power, electrical signals, and/or optical signals.

The attachment interface 2310 is a face of the surgical tool holder 2308 that attaches to the surgical tool. The attachment interface 2310 includes a first portion of an attachment mechanism that reciprocally mates with a second portion of the attachment mechanism located on the surgical tool. The attachment interface 2310 is further described in U.S. Pat. No. 10,470,830, titled SYSTEM AND METHODS FOR INSTRUMENT BASED INSERTION ARCHITECTURES, issued Nov. 12, 2019, for example.

Various tools can attach to the tool driver 2300, including tools used for laparoscopic, endoscopic and endoluminal surgery. Tools can include tool-based insertion architectures that reduce the reliance on robotic arms for insertion. In other words, insertion of a surgical tool (e.g., towards a surgical site) can be facilitated by the design and architecture of the surgical tool. For example, in some instances, wherein a tool comprises an elongated shaft and a handle, the architecture of the tool enables the elongated shaft to translate longitudinally relative to the handle along an axis of insertion. Various advantages of tool-based insertion architectures are further described in U.S. Pat. No. 10,470,830, titled SYSTEM AND METHODS FOR INSTRUMENT BASED INSERTION ARCHITECTURES, issued Nov. 12, 2019, which is incorporated by reference herein its entirety.

A surgical tool 2400 having a tool-based insertion architecture is shown in FIG. 6. Various aspects of the surgical tool 2400 are further described in U.S. Pat. No. 10,470,830, titled SYSTEM AND METHODS FOR INSTRUMENT BASED INSERTION ARCHITECTURES, issued Nov. 12, 2019, for example. The surgical tool 2400 enables a translation of the surgical tool 2400 (e.g., translation of its shaft 2402 and end effector 2412 relative to a tool driver and/or distal end of the robotic arm) along an insertion axis. In such instances, the surgical tool 2400 can be moved along the insertion axis without reliance—or with less reliance—on movement of a robotic arm. The surgical tool 2400 includes an elongated shaft 2402, an end effector 2412 connected to the shaft 2402, and a handle 2420, which may also be referred to as an instrument housing or base, coupled to the shaft 2402. The elongated shaft 2402 comprises a tubular member and includes one or more channels or grooves 2404 along its outer surface. The grooves 2404 are configured to receive one or more wires or cables 2430 therethrough. The cables 2430 run along an outer surface of the elongated shaft 2402. In other aspects of the present disclosure, certain cables 2430 can run through the shaft 2402 and may not be exposed. Manipulation of the cables 2430 (e.g., via the tool driver 2300) results in actuation of the end effector 2412, for example.

The end effector 2412 can include laparoscopic, endoscopic, or endoluminal components, for example, and can be designed to provide an effect to a surgical site. For example, the end effector 2412 can comprise a wrist, grasper, tines, forceps, scissors, clamp, knife, and/or fasteners. Exemplary surgical end effectors are further described herein. The cables 2430 that extend along the grooves on the outer surface of the shaft 2402 can actuate the end effector 2412. The cables 2430 extend from a proximal portion of the shaft 2402, through the handle 2420, and toward a distal portion of the shaft 2402, where they actuate the end effector 2412.

The instrument housing 2420 includes an attachment interface 2422 having one or more mechanical inputs 2424, e.g., receptacles, pulleys or spools, that are designed to be reciprocally mated with one or more torque couplers 2314 (FIG. 5) on the attachment interface 2310 of the tool driver 2300. The attachment interface 2422 is capable of attaching to the tool driver 2300 via a front-mount, back-mount and/or top mount. When physically connected, latched, and/or coupled together, the mated mechanical inputs 2424 of the instrument handle 2420 may share axes of rotation with the torque couplers 2314 of the tool driver 2300, thereby allowing the transfer of torque from the motors in the tool driver 2300 to the instrument handle 2420. In some instances, the torque couplers 2314 may comprise splines that are designed to mate with receptacles on the mechanical inputs. Cables 2430 that actuate the end effector 2412 engage the receptacles, pulleys, or spools of the handle 2420, such that the transfer of torque from the tool driver 2300 to the instrument handle 2420 results in actuation of the end effector 2412.

The surgical tool 2400 can include a first actuation mechanism that controls actuation of the end effector 2412. The surgical tool 2400 can also include a second actuation mechanism that enables the shaft 2402 to translate relative to the handle 2420 along an axis of insertion A. One or more additional actuation mechanism can effect articulation of the end effector 2412 relative to the shaft 2402. For example, the surgical tool 2400 can include an articulation joint 2416, which can allow articulation of the end effector 2412 relative to the shaft 2402 about one or more axes.

In various instances, an actuation mechanism can include one or more pulleys mounted on a rotary axis to change relative cable length and, in other instances, mounting a pulley on a lever, gear or track-based system to adjust its location. Additionally or alternatively, ball spline rotary shafts that travel down a length of a tool can also be used to transmit forces in a mechanically-remote way. Various actuation mechanisms are further described in U.S. Pat. No. 10,470,830, titled SYSTEM AND METHODS FOR INSTRUMENT BASED INSERTION ARCHITECTURES, issued Nov. 12, 2019, for example.

In various instances, the surgical tool 2400 can be a surgical stapler, disposable loading unit, or stapling assembly for cutting and stapling tissue. The surgical stapler can integrally include or be adapted to receive one or more staple cartridges (e.g. a replaceable staple cartridge) therein. A staple cartridge can include multiple longitudinal rows of staple cavities and a longitudinal knife slot, in certain instances. Staples are contained within the staple cavities and are configured to be sequentially fired during a firing stroke (e.g. a proximal-to-distal firing stroke) of a firing member (e.g. an E-beam or I-beam) through the staple cartridge. In various instances, a rotary drive shaft can transmit the firing forces to the firing member. For example, rotation of the rotary drive shaft in the end effector can move the firing member during the firing stroke to engage a sled, staple drivers, and/or staple drivers and to drive the staples into tissue.

Figure 7:
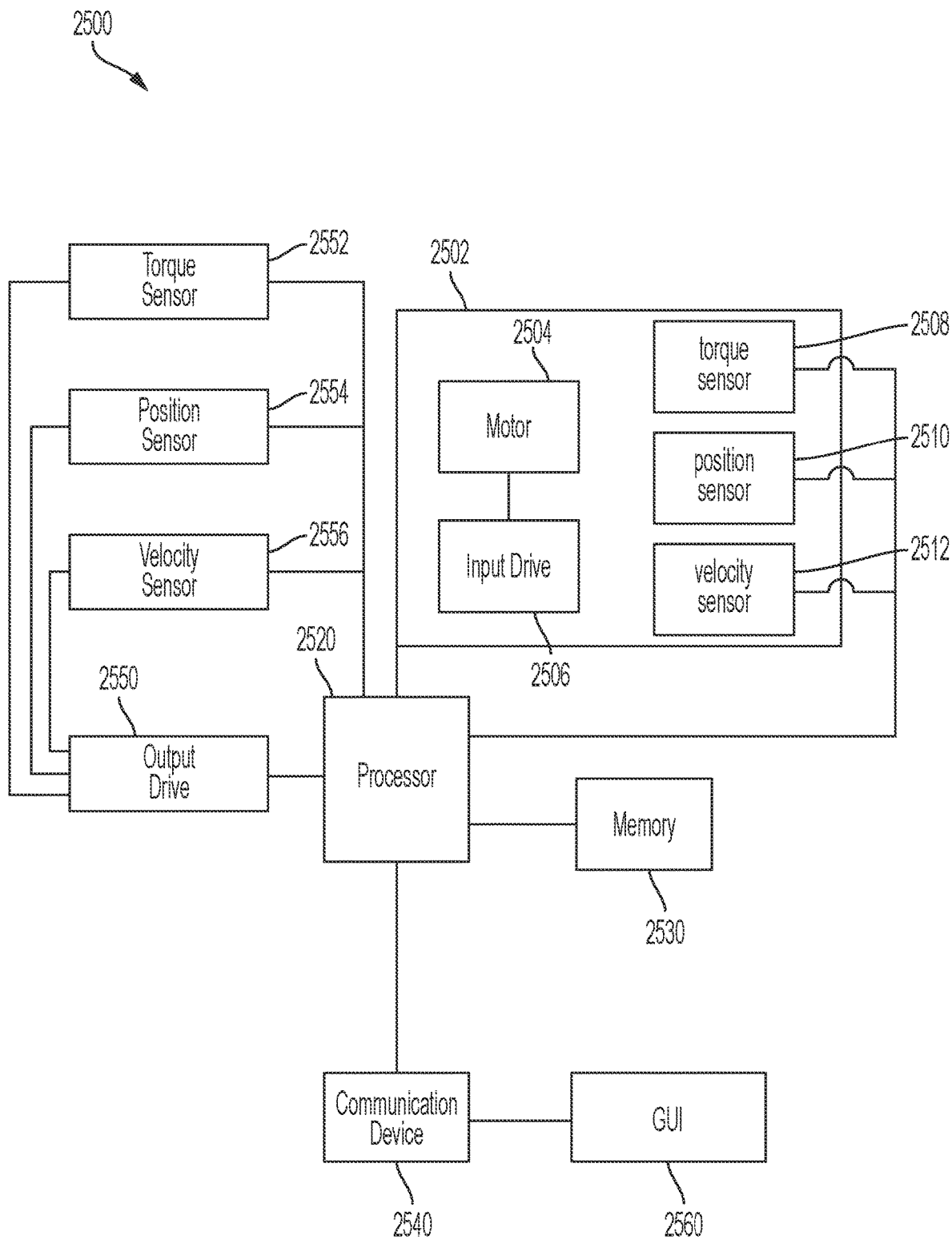
FIG. 7 is a schematic of a control circuit for operating a robotic tool, in accordance with at least one aspect of the present disclosure.

Referring to FIG. 7, various robotic surgical tools, such as the surgical tool 2400 (FIG. 6), for example, can be controlled by a control circuit 2500 and can be used in conjunction with a robotic surgical system, such as the robotic surgical system 2100 (FIG. 1) and with the robotic arm 2212 (FIGS. 3 and 4) and the tool drivers 2275 (FIG. 3), 2285 (FIG. 4), 2300 (FIG. 5), for example. The control circuit 2500 may be in communication with one or more load/torque sensors, one or more encoders, and/or one or more velocity sensors, such as a torque sensor 2508, a rotary encoder/position sensor 2510, and a velocity sensor 2512. The load/torque sensor(s), position sensors(s), and/or velocity sensor(s) can be monitoring devices, which are configured to monitor operational parameters of the robotic surgical tool. The load sensor can be a torque sensor, for example, which may be configured to monitor torque delivered by the motor. The position sensors may be configured to monitor motion/displacement (rotational/rotary or linear), and the velocity sensors may be configured to monitor speed (rotational or linear). In certain instances, a position sensor can comprise an arrangement of one-dimensional position sensors configured to cooperate to determine the three-dimensional coordinates. In certain instances, the three-dimensional coordinates can be calculated with inverse kinematics. The torque sensors, the position sensors, and velocity sensors can be incorporated into the motors of some or all of the tool drivers. Additionally or alternatively, torque sensors, position sensors, and/or velocity sensors can be operatively coupled to one or more of the rotary output drives on the tool base, as further described herein.

The torque sensors may be configured to measure the real-time torque loading on the motors, which corresponds to the torque loading by the drive outputs and applied to the drive inputs, in various instances. The rotary encoders may measure the rotational motion or output of the motors, which corresponds to the rotational motion of the drive outputs and/or the drive inputs. The velocity sensors may measure the rotational velocity of the motors, which corresponds to the rotational velocity of the driver outputs and/or the drive inputs. Monitoring torque loading, rotational motion, and rotational velocity of the motors may help determine if the robotic surgical tool 2400 is operating in accordance with the commands provided by the control circuit.

The control circuit 2500 in FIG. 7 is for controlling one of the motors in a tool base. In various instances, the control circuit 2500 can control all of the motors in a similar manner so only one motor 2504 is shown in FIG. 7. The control circuit 2500 can be implemented as a non-transitory computer readable medium storing computer readable instructions. The non-transitory computer-readable medium can include any type of tangible machine-readable medium suitable for storing or transmitting electronic instructions or information in a form readable by a machine (e.g., a computer), which can be logic for operating the control circuit 2500. The control circuit 2500 includes a processor 2520 in signal communication with a memory 2530 and with a communication device 2540. The communication device can be connected to a graphical user interface (GUI) 2560, where a user can receive information from the processor 2520 and provide inputs. A first drive system 2502 is in signal communication with the processor 2520. The first drive system 2502 includes a motor 2504, a drive 2506 coupled to the motor 2504, a torque sensor 2508, a rotary encoder/position sensor 2510, and a velocity sensor 2512. The drive 2506 can correspond to one of the drive outputs 2314 (FIG. 5), which provides a drive input to a robotic surgical tool coupled thereto, for example.

The control circuit 2500 can also include a tool drive 2550, a torque sensor 2552, a rotary encoder/position sensor 2554, and a velocity sensor 2556. The tool drive 2550 can correspond to any joint that is moved on the surgical tool, for example. In such instances, the torque sensor 2552 determines the output torque applied to the joint, the position sensor 2554 determines the angular position of the joint, and the velocity sensor determines the angular velocity of the joint.

The processor 2520 can be programmed and otherwise configured to monitor operation of the surgical tool 2400 (FIG. 6) using various sensors and/or electromechanical devices, including the various torque sensors, position sensors, and velocity sensors described herein. Various monitoring devices in signal communication with a processor are further described in U.S. Patent Application Publication No. 2021/0093409, titled COMMUNICATING CLOSURE EFFORT FOR ROBOTIC SURGICAL TOOLS BACKGROUND, which published Apr. 1, 2021, which is incorporated by reference herein in its entirety. Based on measurements acquired by the various sensors, the processor 320 can be programmed and otherwise configured to calculate the work or effort required to grasp tissue with the jaws of the end effector 2412 (FIG. 6). The processor 2520 may further be programmed and otherwise configured to communicate the amount of real-time grasping work (effort) completed to the operator (e.g., the surgeon) in the form of an effort indicator (also referred to as a communication device) 2540. The effort indicator 2540 can be provided to the operator using any form of sensory feedback, such as auditory feedback, tactile feedback, visual feedback via a graphical user interface 2560, or any combination thereof. Providing real-time effort indicators may provide the operator with a consistent and reliable replacement for the tactile feedback common to manually operated surgical tools but absent in robotic surgical tools and/or motor-driven grasping motions. By receiving the effort indicators in real-time, the operator can repeatedly grasp the tissue to get the general "feel" of potential target tissue based on the effort indicators provided by the processor 2520.

In some cases, the magnitude of the effort indicator 2540 (e.g., auditory or tactile feedback, or shape of a visual feedback) with respect to grasp motor effort could indicate tissue properties. For example, a visual effort indicator profile of healthy tissue could rise sharply, then settle out to a final value in certain instances. A visual effort indicator profile of diseased tissue could gradually rise to the same final value as the healthy tissue. The healthy and diseased tissue samples may comprise, for instance, samples of the same portion of an organ (from different patients), irradiated vs. non-irradiated tissue, scarred vs. unscarred tissue, etc. The resulting visual effort indicator profiles, in addition to the magnitude, could indicate tissue properties.

Figure 8A:
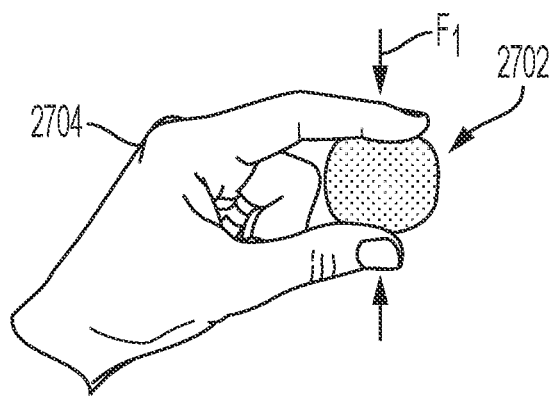
FIGS. 8A and 8B depict progressive operation of a user input device, in accordance with at least one aspect of the present disclosure.
Figure 8B:
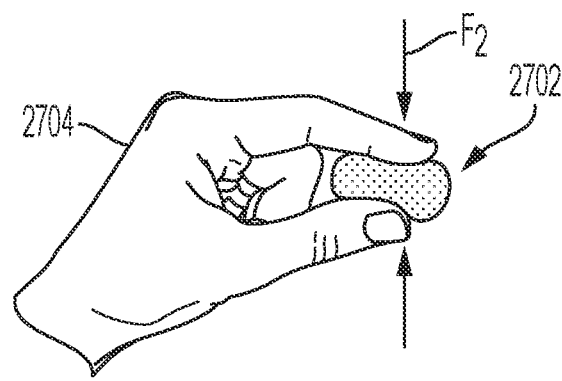

FIGS. 8A and 8B depict progressive operation of an example user input device 2702 used to move, articulate, and/or actuate the surgical tool 2400 (FIG. 6) and/or the end effector 2412 (FIG. 6). As indicated above, example user input devices that may be used in a robotic surgical system can include hand-held actuator modules, a joystick, exoskeletal gloves, a master manipulator, or any combination thereof. In FIGS. 8A and 8B, the user input device (UID) 2702 comprises a type of hand-held actuator module that can be communicably coupled, either wired or wirelessly, to the master control console (e.g. console 2116 in FIG. 1) of the robotic surgical system. Any physical manipulation of the UID 2702 by the clinician (e.g., surgeon) will be recognized by the master control console and result in movement, articulation, and/or actuation of the surgical tool 2400 and/or the end effector 2412.

As illustrated, the UID 2702 can be grasped with the operator's hand 2704, such as between the forefinger and the thumb of the hand 2704. While grasped by the operator's hand 2704, the UID 2702 may be moved in multiple degrees of freedom to control the position of the end effector 2704 (FIG. 4) relative to a surgical site. Moreover, the operator may be able to squeeze (compress) the UID 2702 to cause actuation of the end effector 2414, such as clamping with the jaws. More specifically, squeezing the UID 3602 between the forefinger and the thumb of the hand 2704 (or any other portion of the hand 3604) may generate corresponding signals sent to the processor 2520 (FIG. 7) to cause operation (e.g., rotation) of the rotary drivers 2314 (FIG. 5), which drive corresponding drive inputs on the robotic tool 2400 to open and close the jaws of the end effector 2412 (FIG. 6).

In at least one aspect of the present disclosure, the resulting closing and grasping force applied at the jaws by the robot will depend on how hard the operator squeezes the UID 2702. In FIG. 8A, for example, the UID 2702 is shown being squeezed between the forefinger and thumb of the hand 2704 with a first force $F_1$, which equates to a proportional amount of force applied at the jaws by the robotic surgical system. In FIG. 8B, the UID 2702 is squeezed with a second force $F_2$ that is greater than the first force $F_1$, which equates to a greater proportional amount of force applied at the jaws by the robotic surgical system.

As the operator manipulates (squeezes) the UID 2702 (FIGS. 8A and 8B), the sensors measure the torque and the rotational angle, respectively, of the motor 2504 (or motors in certain instances), and report these measurements to the processor 2520 in real-time. Based on the torque and the rotational angle measurements provided by the sensors, the processor 2520 can be programmed and otherwise configured to calculate the work completed by the motor(s) in closing the jaws. One or more real-time effort indicators indicative of the amount of grasping work completed by the jaws may then be generated and communicated to the operator (e.g., the surgeon).

Figure 9:
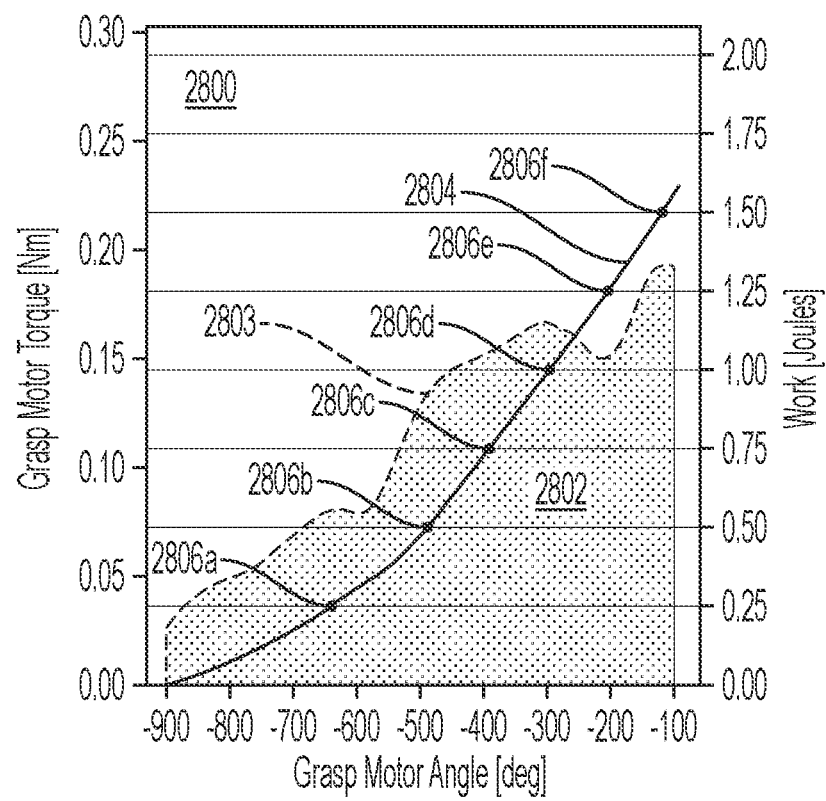
FIG. 9 depicts an example plot generated by the processor of FIG. 7 based on torque and rotational angle measurements, in accordance with at least one aspect of the present disclosure.

FIG. 9 is an example plot 2800 generated by the processor 2520 (FIG. 7) based on torque and rotational angle measurements obtained by the sensors (FIG. 7), respectively. More specifically, the plot 2800 depicts an area 2802 representative of the torque vs. the rotational angle measured on the motor(s) (e.g. the motor 2504 (FIG. 7)) while grasping the jaws on tissue. By taking the integral of an upper boundary 2803 of the area 2802, work 2804 completed by the motor(s) may be determined (calculated) and is represented on the plot 2800 in the form of a line.

One or more predetermined work increments corresponding to operation of the motor(s) may be set. If the measured work 2804 meets or exceeds a predetermined work increment, the processor 2520 (FIG. 7) can be programmed to communicate a corresponding effort indicator to the operator in real-time indicative of the amount of grasping work completed. In the illustrated embodiment, for example, predetermined work increments 2806 comprise work increments of a set magnitude of 0.25 Joules, which are indicated on the plot 2800 as predetermined work increments 2806*a*, 2806*b*, 2806*c*, 2806*d*, 2806*e*, and 2806*f*. As the work 2804 completed by the motor(s) meets or surpasses (exceeds) any of the predetermined work increments 2806*a-f*, the processor 2520 (FIG. 7) can communicates a corresponding effort indicator to the operator in real-time to indicate that the amount of grasping work has met the particular predetermined work increment 2806*a-f*. As will be appreciated, the work increments of the set magnitude can be any magnitude, without departing from the scope of the disclosure.

In some embodiments, the predetermined work increments 2806*a-f* may alternatively comprise a percentage of the total work possible for the motor(s) to fully close the jaws and grasp onto tissue. For example, if grasping and fully closing the jaws requires fifteen (15) radians of angular movement for the motor(s) and can use up to 0.5 Nm of torque, then the total possible work for the jaws to fully close and grasp onto tissue is 7.5 joules. In such embodiments, the predetermined work increments 2806*a-f* could be set in increments of 5%, 10%, 15%, etc. of 7.5 joules, or any other desired multiple percentage. As the work 2804 completed by the motor(s) meets or surpasses (exceeds) any of the set percentages as predetermined work increments 2806*a-f*, the processor 2520 (FIG. 7) can communicate a corresponding effort indicator to the operator.

In some embodiments, the work 2804 may only increase in one angular direction of motor travel. In such embodiments, travel of the motor in the opposite angular direction may reset the calculation for the calculated work 2804. As will be appreciated, resetting the calculation for the calculated work 2804 upon reversal of the motor(s) prevents combining the work calculated for a first grasp event with that of a second. As further described herein, the work calculation can be paused or reset in alternative circumstances in various aspects of the present disclosure.

The effort indicators may be provided to the operator in the form of sensory feedback that can be recognized by at least one of the operator's senses. In some embodiments, for example, the effort indicator may comprise auditory (audible) feedback that can be heard by the operator. In other embodiments, the effort indicators may comprise tactile feedback that can be physically felt by the operator. In some embodiments, the effort indicators may comprise a combination of audible and tactile feedback, such as a vibration and a click or sound being generated simultaneously and communicated to the operator. In yet other embodiments, the effort indicators may comprise visual feedback that can be seen (viewed) by the operator. The visual feedback may be provided to the operator in a variety of ways. In some embodiments, the effort indicators may comprise a combination of audible, tactile, and visual feedback, or any combination thereof. Various types of feedback are further described in U.S. Patent Application Publication No. 2021/0093409, titled COMMUNICATING CLOSURE EFFORT FOR ROBOTIC SURGICAL TOOLS BACKGROUND, which published Apr. 1, 2021, which is incorporated by reference herein in its entirety.

In various instances, communicating the current and previous work 2804 (FIG. 8) values may prove advantageous in determining tissue characteristics and/or helping the clinician understand the type of tissue being grasped. For example, feedback related to the work can replace the loss of tactile feedback clinician's experience when using a handheld surgical grasping tool and/or surgical stapler. For example, when a surgical robot is performing the work during a clamping motion, the clinician can be unaware of the amount of effort required to clamp the tissue. However, the work or effort required of the surgical robot during the clamping motion can provide clinical insight with respect to a subsequent clamping and/or firing stroke.

In certain instances, grasping work can be calculated for each piece of tissue. When the end effector is opened, relocated, repositioned, and/or reoriented to grasp a different piece of tissue, the grasping work calculation can be reset. In such instances, work calculations for different locations of tissue are separate calculations rather than a combined total across tissue locations, and the grasping work calculations can account for end effector stability and distinguish between different pieces of tissue.

Figure 10:
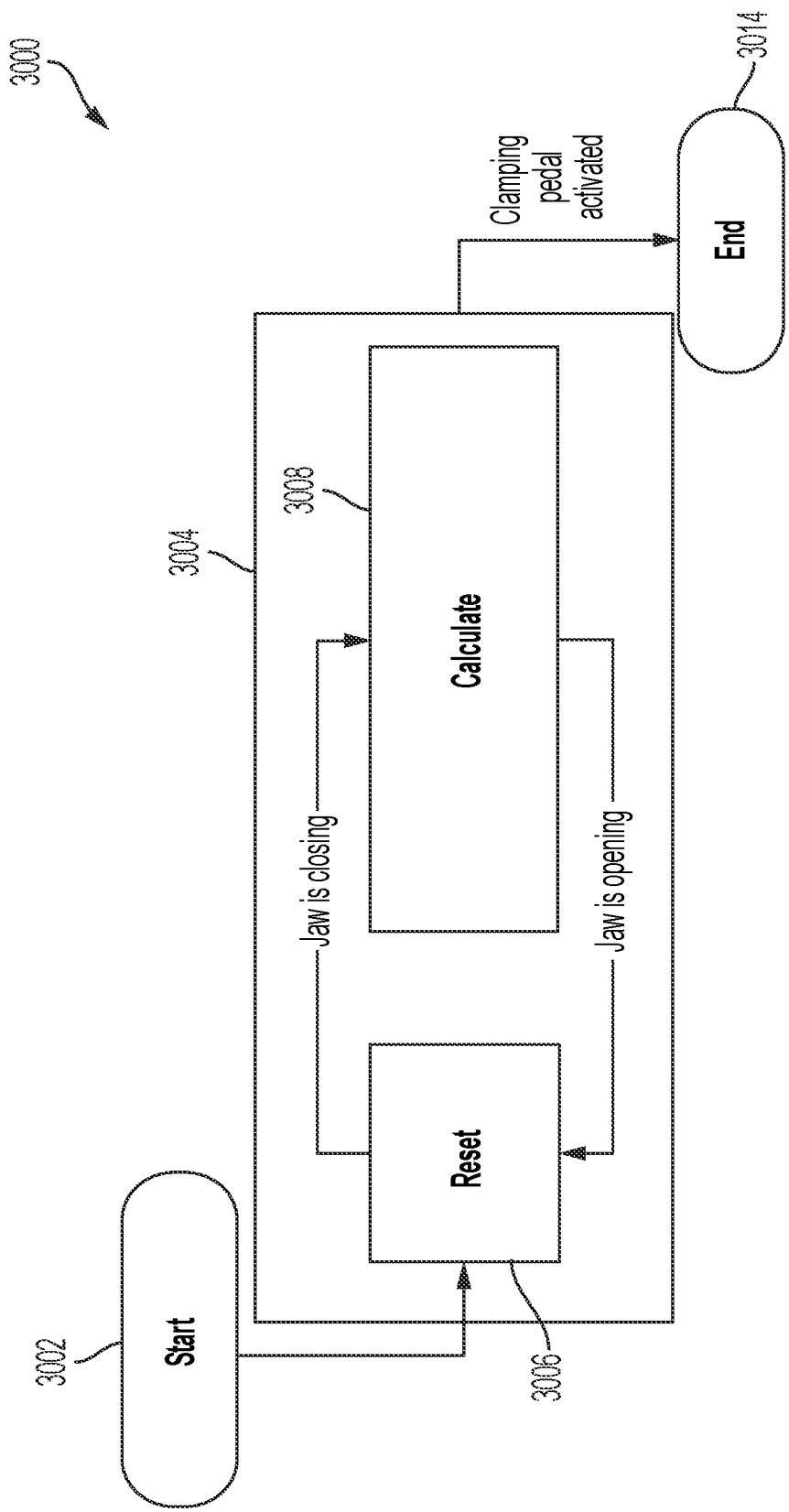
FIG. 10 is a logic diagram depicting a work calculation flowchart, in accordance with at least one aspect of the present disclosure.

Referring now to FIG. 10, a flowchart 3000 depicts work calculation logic for a robotic system and a robotic tool thereof, such as the robotic system 2100 (FIG. 1) and the robotic tool 2400 (FIG. 6), for example. The flowchart 3000 can be implemented by a control circuit, such as the control circuit 2500 (FIG. 7), in certain instances. In various instances, the flowchart 3000 can be implemented as a non-transitory computer readable medium storing computer readable instructions, and the non-transitory computer-readable medium can include any type of tangible machine-readable medium suitable for storing or transmitting electronic instructions or information in a form readable by a machine (e.g., a computer), which can implement the transitions between states in the flowchart 3000. In various instances, a memory for a robotic surgical system, such as the memory 2530 (FIG. 7) can store program instructions for performing the work calculation logic in the flowchart 3000, and a processor, such as the processor 2520 (FIG. 7) can be configured to execute the logic and steps of the flowchart 3000.

An outset (or start) 3002 of the flowchart 3000 can follow completion of a homing operation. At the outset 3002, the robotic system can enter a grasping mode 3004, in which one or both of the jaws of the end effector, such as jaws of the end effector 2412 (FIG. 6), for example, are closed in teleoperation to grasp patient tissue. User input via a UID, such as the UID 2702 (FIGS. 8A and 8B), can transmit a signal initiating jaw closure, for example. In the grasping mode 3004, the grasping work can initially be reset at a reset state 3006. In the reset state 3006, the grasping work calculation can be reset (e.g. set to zero).

From the reset state 3006, the flowchart 3000 then transitions to a calculate state 3008, in which the grasping work is calculated. The grasping work can be calculated in the calculate state 3008 for each time-step or area under the curve of torque versus angle, where torque and angle are measured in real-time from the closure/grasping motor(s). In various instances, the grasping work can be calculated by taking the integral of torque detected by a torque sensor coupled to the motor over the angular displacement detected by a rotary output of the motor. In certain instances, both jaws can move (e.g. pivot) to clamp tissue. At least one motor can drive each jaw and, in certain instances, the motor(s) can be coupled to a corresponding torque sensor and rotary encoder, as further described herein. In other instances, one jaw can be a fixed jaw and the other jaw can be a movable jaw. At least one motor can drive the movable jaw and a torque sensor and rotary encoder can be coupled to the motor(s). When multiple motors are used to close the jaws, the work of each motor for each time-step during the calculate state 3008 is combined/summed and added to the grasp work calculation.

If the jaw(s) of the end effector begin to open, the flowchart 3000 transitions to the reset state 3006. Upon reentering the reset state 3006, the work calculation is again zeroed. As the jaws of the end effector close, the flowchart 3000 resumes or returns to the calculate state 3008 from the reset state 3006. In such instances, the flowchart 3000 is configured to distinguish between grasping events, e.g. grasping on different pieces of tissue.

Opening and closing of the jaw(s) can be determined by the rotary direction of a position sensor for the motor(s) (e.g. rotary encoder 2510 in FIG. 7). For example, a change in rotary direction from a closing direction of the closure motor to an opening direction indicates opening of the jaws. In various instances, the angle of the closure motor is measured by a position sensor (e.g. rotary encoder 2510) and the angle is recorded/stored in memory. If the next measured angle is less than or equal to the stored angle, the motor is determined to be closing the jaw. If the next measured angle is greater than or equal to the stored angle, the motor is consider to be opening the jaw.

The flowchart 3000 and work calculations thereof can continue throughout the grasping mode 3004 until an end (or termination) 3014 of the grasping mode 3004. In various instances, feedback can be transmitted to a GUI or alternative feedback device during the grasping mode 3004 to provide up-to-date and real-time (or near real-time) work calculations to the clinician. Upon exiting the grasping mode 3004, the final grasping work calculation(s) can be transmitted and/or recorded. Activation of a clamping actuator, such as a clamping pedal, for example, can terminate the grasping mode 3004 and initiate a clamping mode 3004 in various instances. In other instances, a user input can terminate the grasping mode 3004 without initiating a clamping mode. For example, the clamping mode 3004 can be circumvented in response to a determination of certain unexpected tissue characteristics during the grasping mode 3004, which may necessitate a modification to the surgical plan, for example.

Figure 11:
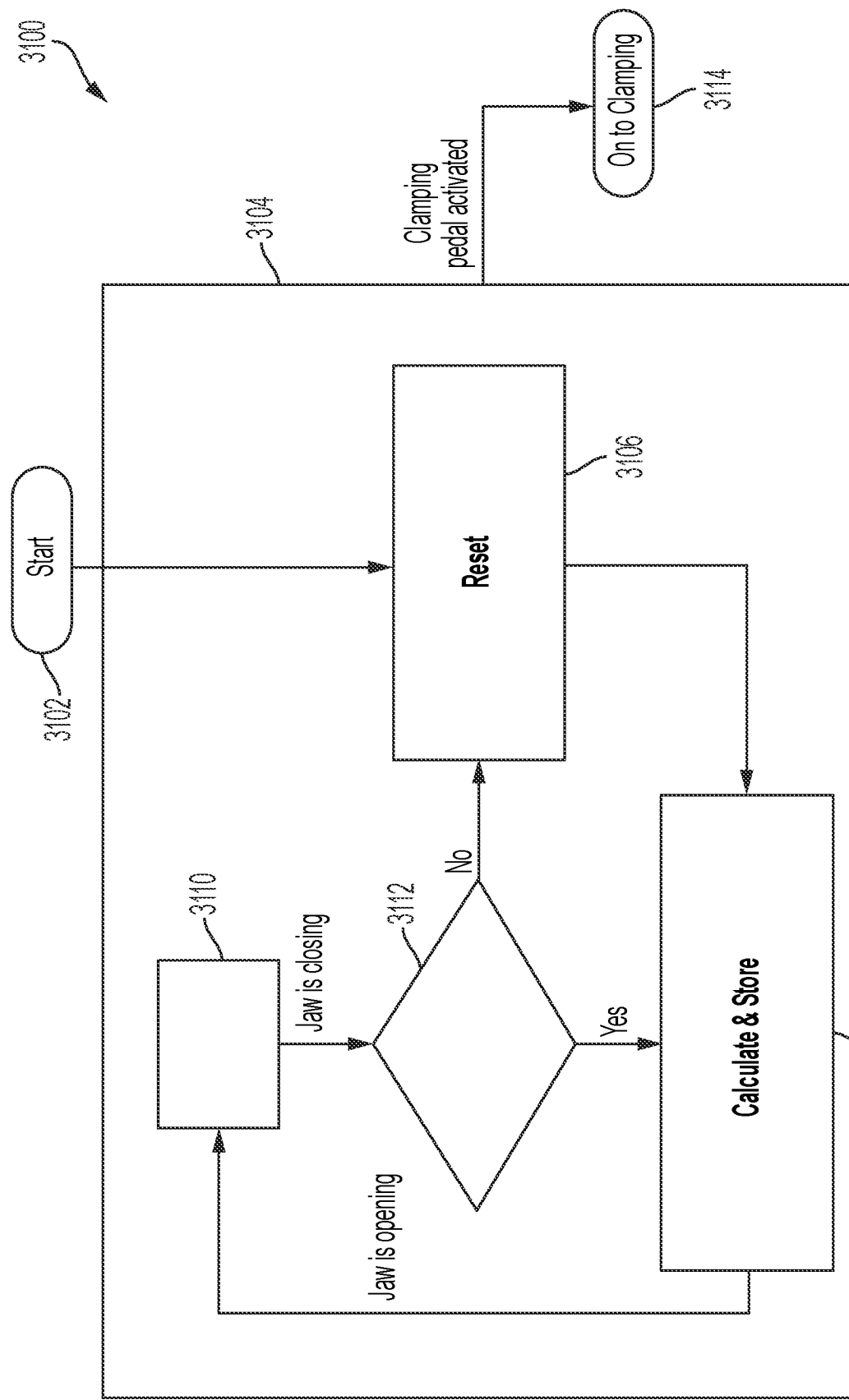
FIG. 11 is a logic diagram depicting a work calculation flowchart, in accordance with at FIG. 11 is a logic diagram depicting a work calculation flowchart, in accordance with at least one aspect of the present disclosure.

Referring now to FIG. 11, a flowchart 3100 depicts work calculation logic for a robotic system and a robotic tool thereof, such as the robotic system 2100 (FIG. 1) and the robotic tool 2400 (FIG. 6), for example. The flowchart 3100 is similar in many aspects to the flowchart 3000; however, the work calculation is reset when the jaw has been opened a threshold amount after an initial closure motion corresponding to an initial work calculation. The flowchart 3100 can be implemented by a control circuit, such as the control circuit 2500 (FIG. 7). In various instances, the flowchart 3100 can be implemented as a non-transitory computer readable medium storing computer readable instructions, and the non-transitory computer-readable medium can include any type of tangible machine-readable medium suitable for storing or transmitting electronic instructions or information in a form readable by a machine (e.g., a computer), which can implement the transitions between states in the flowchart 3100. In various instances, a memory for a robotic surgical system, such as the memory 2530 (FIG. 7) can store program instructions for performing the work calculation logic in the flowchart 3100, and a processor, such as the processor 2520 (FIG. 7) can be configured to execute the logic and steps of the flowchart 3100.

At the outset (or start) 3102 of the flowchart 3100, the robotic system can enter a grasping mode 3104, in which one or both of the jaws of the end effector are closed in teleoperation to grasp patient tissue. In the grasping mode 3104, the grasping work can initially be reset at a reset state 3106. In the reset state 3106, the grasping work calculation can be reset (e.g. set to zero). Moreover, the jaw angle value can be reset (e.g. set to zero). In certain instances, the position of the end effector and the orientation of the end effector can be recorded or stored. The stored position can be set to the current Cartesian coordinates of the end effector (e.g. x, y, and z coordinates), which can be determined by inverse kinematics of a robotic arm, for example. The stored orientation can be set to the current orientation of the end effector (e.g. yaw, pitch, and roll values), which can also be determined by inverse kinematics of the robotic arm, for example.

The flowchart 3100 then transitions to a calculate state 3108, in which the grasping work is calculated. The grasping work can be calculated in the calculate state 3108 for each time-step or area under the curve of torque versus angle, where torque and angle are measured in real-time from the closure/grasping motor(s). In various instances, the grasping work can be calculated by taking the integral of torque detected by a load sensor coupled to each motor (e.g. the torque sensor 2508 in FIG. 7) over the angular displacement detected by a respective rotary output of the motor (e.g. the rotary encoder 2510 in FIG. 7). In the calculate state 3108, the grasp angle of the jaw is stored.

If one or both jaws of the end effector begins to open, the flowchart 3100 transitions to a pause state 3110, in which the work calculation summation is paused. In the pause state 3110, the work calculation is held at its last and most-recent value and the flowchart 3200 remains in the pause state 3110 until the jaw(s) again begin to close. Determination of an opening jaw motion versus a closing jaw motion is further described herein.

As the jaws of the end effector close, the flowchart 3100 resumes or returns to the calculate state 3108 if a closure angle determination 3112 of the end effector is "yes" or positive. If the closure angle determination 3112 is "no" or negative, the flowchart 3100 transitions to the reset state 3106, in which the grasping work is reset. The closure angle determination 3112 depends on the closure angle of the jaw. When the closure angle is similar to the most recent jaw angle value (i.e. within a predefined/stored range of values) recorded/stored during the calculate state 3108 before the jaw started to open, the closure angle determination 3112 is yes. However, when the closure angle is dissimilar to the jaw angle value (i.e. outside the predefined/stored range of values) recorded/stored during the calculate state 3108, the closure angle determination 3112 is no.

The flowchart 3100 ensures that the work calculation accumulates while the jaws are closing and the work calculation is only reset when the jaw angle is sufficiently different from the last jaw angle stored in the calculate state 3108 at the point of first opening of the jaw. In such instances, small variations and/or insignificant opening motions do not trigger a reset of the grasping work calculations. However, opening of the jaw(s) a threshold amount, degree, and/or percentage of the closure arc length indicates that a first grasping event has ended and a second grasping event may begin. The threshold difference between the jaw angles can be selected to avoid resetting the work calculation based on minor measurement errors and/or differing of the jaws during the clamping state 104.

The flowchart 3100 and work calculations thereof can continue throughout the grasping mode 3104 until an end (or termination) 3114 of the grasping mode 3104. In various instances, feedback can be transmitted to a GUI or alternative feedback device during the grasping mode 3104 as further described herein. Activation of a clamping actuator, such as a clamping pedal, for example, can terminate the grasping mode 3104 and initiate a clamping mode 3104 in various instances and, in other instances, a user input can terminate the grasping mode 3104 without initiating a clamping mode, as further described herein.

In various aspects of the present disclosure, the work can be continually calculated while the jaws are closing. The work can be additively stored only when the work is increasing, and the initial jaw angle can be stored only where the work is greater than zero. The work calculation algorithm can remain in the continual calculation state until opening of the jaw(s) is detected. While the jaws are opening, the jaw angle can be compared to the initial jaw angle and, if the jaw angle is greater than the initial jaw angle, the grasping work can be reset. Upon re-closure of the jaws, the continual calculation mode can again be initiated.

Figure 12:
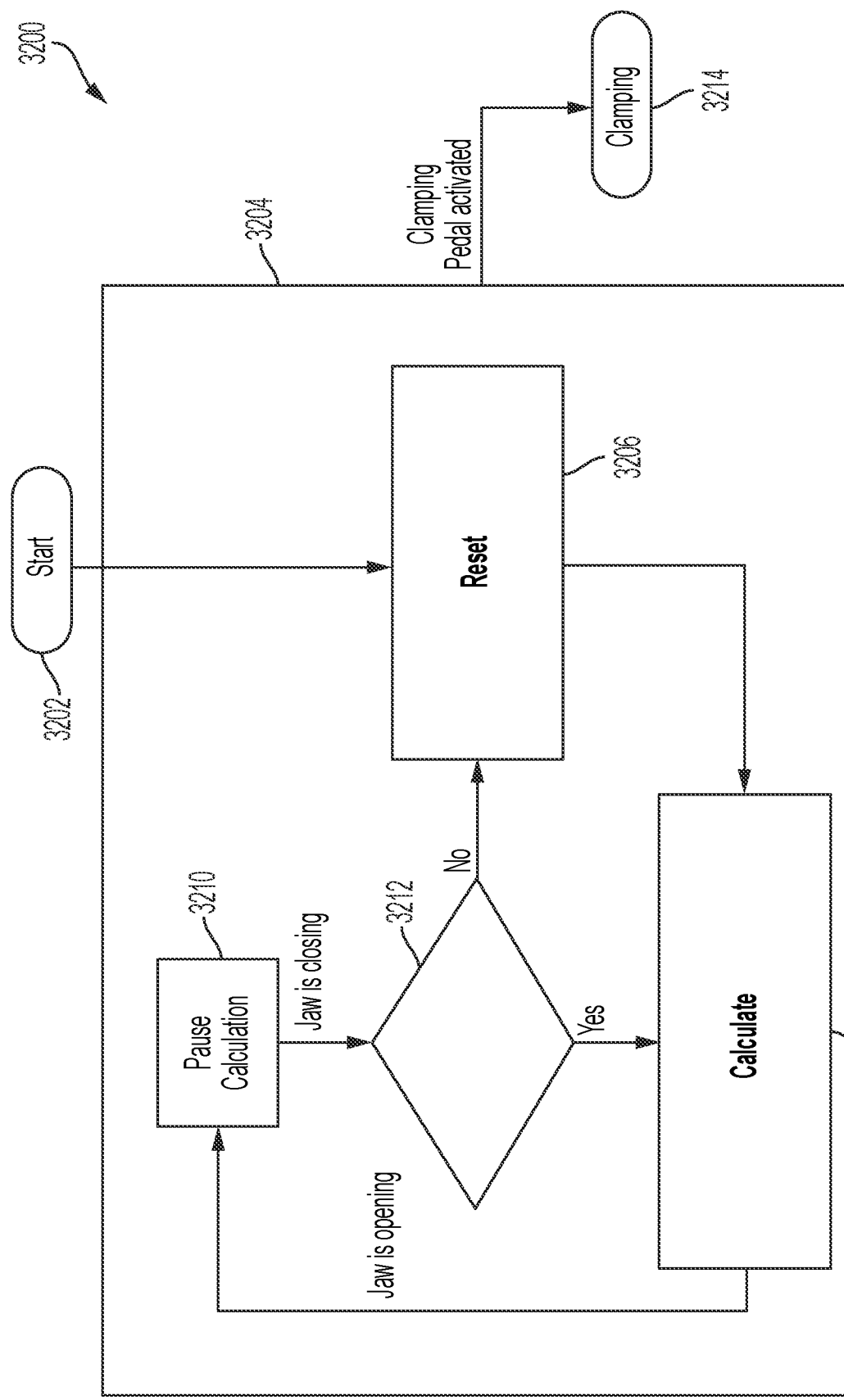
FIG. 12 is a logic diagram depicting a work calculation flowchart, in accordance with at least one aspect of the present disclosure.

Referring now to FIG. 12, a flowchart 3200 depicts work calculation logic for a robotic system and a robotic tool thereof, such as the robotic system 2100 (FIG. 1) and the robotic tool 2400 (FIG. 6), for example. The flowchart 3200 is similar in many aspects to the flowchart 3000; however, the work calculation is reset when the end effector has been moved outside a predefined range of positions or three-dimensional zone/space/volume. The flowchart 3200 can be implemented by a control circuit, such as the control circuit 2500 (FIG. 7) in certain instances. In various instances, the flowchart 3200 can be implemented as a non-transitory computer readable medium storing computer readable instructions, and the non-transitory computer-readable medium can include any type of tangible machine-readable medium suitable for storing or transmitting electronic instructions or information in a form readable by a machine (e.g., a computer), which can implement the transitions between states in the flowchart 3200. In various instances, a memory for a robotic surgical system, such as the memory 2530 (FIG. 7) can store program instructions for performing the work calculation logic in the flowchart 3200, and a processor, such as the processor 2520 (FIG. 7) can be configured to execute the logic and steps of the flowchart 3200.

At the outset (or start) 3202 of the flowchart 3200, the robotic system can enter a grasping mode 3204, in which one or both of the jaws of the end effector are closed in teleoperation to grasp patient tissue. In the grasping mode 3204, the grasping work can initially be reset at a reset state 3206. In the reset state 3206, the grasping work calculation can be reset (e.g. set to zero). Moreover, the position of the end effector and the orientation of the end effector can be recorded or stored. The stored position can be set to the current Cartesian coordinates of the end effector (e.g. x, y, and z coordinates), which can be determined by inverse kinematics of a robotic arm, for example. The stored orientation can be set to the current orientation of the end effector (e.g. yaw, pitch, and roll values), which can also be determined by inverse kinematics of the robotic arm, for example.

The flowchart 3200 then transitions to a calculate state 3208, in which the grasping work is calculated. The grasping work can be calculated in the calculate state 3208 for each time-step or area under the curve of torque versus angle, where torque and angle are measured in real-time from the closure/grasping motor(s). In various instances, the grasping work can be calculated by taking the integral of torque detected by a load sensor coupled to each motor (e.g. the torque sensor 2508 in FIG. 7) over the angular displacement detected by a respective rotary output of the motor (e.g. the rotary encoder 2510 in FIG. 7).

If one or both jaws of the end effector begins to open, the flowchart 3200 transitions to a pause state 3210, in which the work calculation summation is paused. In the pause state 3210, the work calculation is held at its last and most-recent value for the stored position and orientation of the end effector. The flowchart 3200 remains in the pause state 3210 until the jaw(s) again begin to close. Determination of an opening jaw motion versus a closing jaw motion is further described herein.

As the jaws of the end effector close, the flowchart 3200 resumes or returns to the calculate state 3208 if a stability determination 3212 of the end effector is "yes" or positive. If the stability determination 3212 is "no" or negative, the flowchart 3200 transitions to the reset state 3206, in which the grasping work is reset. The stability determination 3212 depends on the position and orientation of the end effector. When the position and orientation are similar to the recorded/stored values (i.e. within a predefined/stored range of values) during the reset state 3206, the stability determination 3212 is yes. However, when the position and/or orientation of the end effector is dissimilar to the recorded/stored values (i.e. outside the predefined/stored range of values) during the reset state 3206, the stability determination 3212 is no. A three-dimensional volume or space can be defined around the initial stored position and/or orientation of the end effector, and the stability determination 3212 is yes when the end effector remains within the three-dimensional boundary of that volume or space. In certain instances, the volume can accommodate measurement errors and dithering of the end effector during a clamping motion, for example.

The flowchart 3200 ensures that the work calculation accumulates while the jaws are closing and the end effector remains close to the stored position and orientation and, thus, grasping on the same piece of tissue. The work calculation is reset when the end effector is relocated and/or reoriented because such a relocation and/or reorientation indicates the end effector is grasping a different piece of tissue.

The flowchart 3200 and work calculations thereof can continue throughout the grasping mode 3204 until an end (or termination) 3214 of the grasping mode 3204. In various instances, feedback can be transmitted to a GUI or alternative feedback device during the grasping mode 3204 as further described herein. Activation of a clamping actuator, such as a clamping pedal, for example, can terminate the grasping mode 3204 and initiate a clamping mode 3204 in various instances and, in other instances, a user input can terminate the grasping mode 3204 without initiating a clamping mode, as further described herein.

As an example, in at least one aspect of the present disclosure, a surgical system can include an end effector configured to grasp tissue during a grasping motion, a motor configured to drive the grasping motion, a rotary encoder configured to detect rotary positions of the motor; a torque sensor configured to detect torques delivered by the motor; a position sensor configured to detect three-dimensional positions of the end effector. The surgical system can also include a control circuit comprising a processor and a memory communicatively coupled to the processor, wherein the memory stores program instructions executable by the processor to: receive a position parameter from the position sensor, a rotary parameter from the rotary encoder, and a torque parameter from the torque sensor and to store the position parameter at the outset of the grasping motion in the memory. The control circuit is further configured to calculate an amount of work performed by the motor during the grasping motion from the rotary parameter and the torque parameter while the position sensor detects the positon of the end effector remaining within a three-dimensional zone around the position parameter stored at the outset of the grasping motion. The control circuit is further configured to transmit a work signal to a communication device indicative of the amount of work performed by the motor during the grasping motion and to reset the calculation of the amount of work performed by the motor during the grasping motion when the position sensor detects a displacement of the end effector out of the three-dimensional zone around the position parameter stored at the outset of the grasping motion.

In such instances, the control circuit is configured to reset the work calculation when the end effector's position and/or orientation moves outside a range of positions/orientations stored at the outset of the work calculation for a closure motion.

In certain instances, the work calculations may exclude irrelevant grasping work, such as when the jaws of the end effector are grasping air. In the absence of material, such as patient tissue, for example, being positioned between the jaws of the end effector, a grasping motion can merely grasp upon air. Grasping upon air can be associated with a closure motor torque detected by a load sensor (e.g. torque sensor 2508 in FIG. 7) being less than a threshold value. In such instances, the work performed by the motors when grasping air can be ignored by the work/effort calculations.

For example, in one aspect of the present disclosure, a surgical system can comprise an end effector comprising a first jaw and a second jaw, wherein at least one of the first jaw and the second jaw is configured to move through a grasping motion to grasp tissue therebetween; a motor configured to drive the grasping motion; a rotary encoder configured to detect rotary positions of the motor; a torque sensor configured to detect torques delivered by the motor; and a control circuit comprising a processor and a memory communicatively coupled to the processor. The memory can store a nominal torque threshold and program instructions executable by the processor to receive rotary parameters from the rotary encoder and torque parameters from the torque sensor. The program instructions can be further configured to accumulate an amount of work performed by the motor during the grasping motion from the rotary parameters and the torque parameters excluding work performed when the torque parameter is less than the nominal torque threshold and to transmit a work signal to a communication device indicative of the accumulated amount of work.

In such instances, the work performed during portions of the grasping motion can be ignored, such as when the torque is less than a threshold torque corresponding to the amount of torque required for the grasping motion without tissue being positioned between the jaws.

Figure 13:
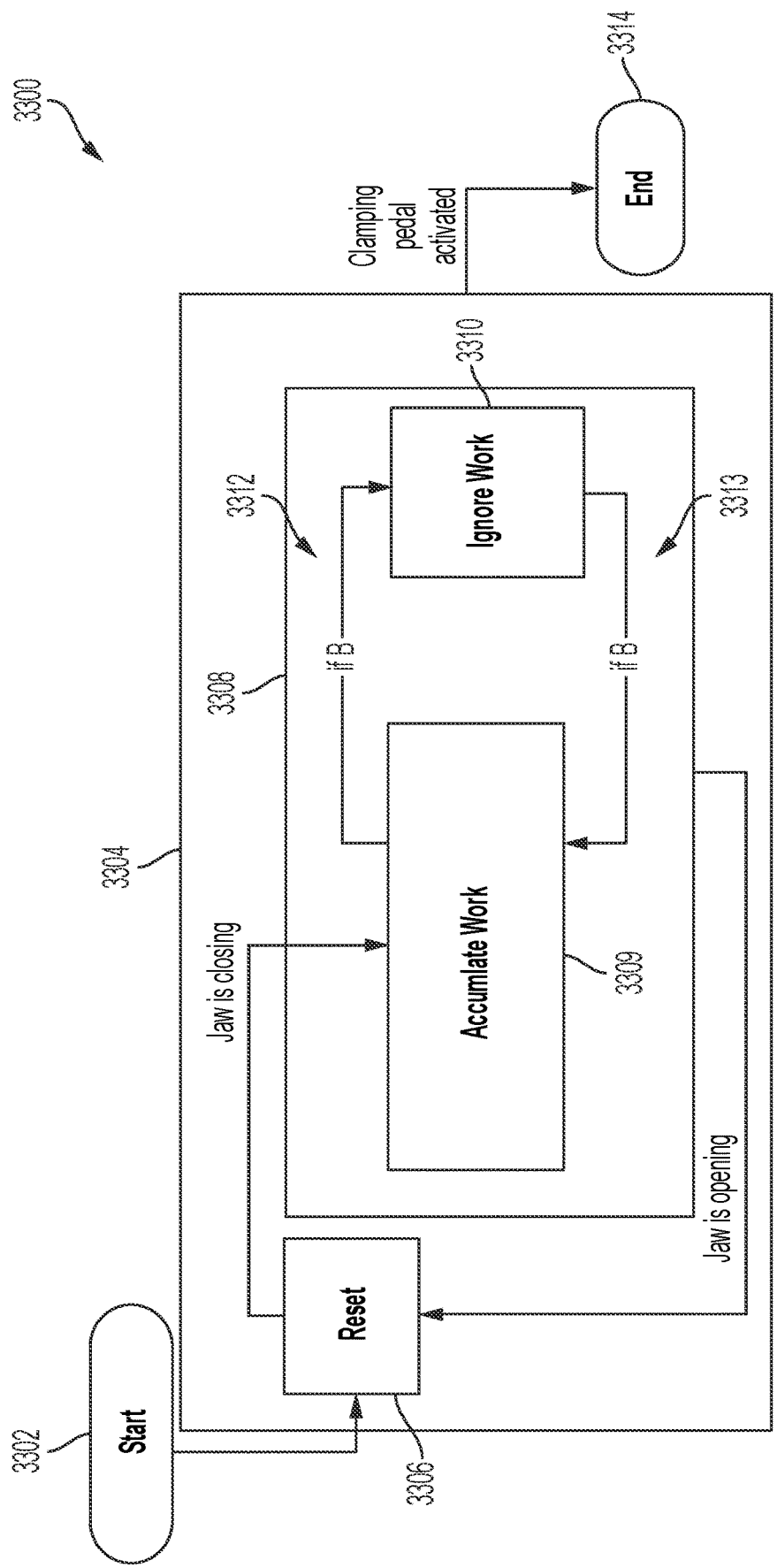
FIG. 13 is a logic diagram depicting a work calculation flowchart, in accordance with at least one aspect of the present disclosure.

Referring now to FIG. 13, a flowchart 3300 depicts work calculation logic for a robotic system and a robotic tool thereof, such as the robotic system 2100 (FIG. 1) and the robotic tool 2400 (FIG. 6), for example. The flowchart 3300 is similar in many aspects to the flowchart 3000; however, the work calculation ignores work performed when the closure motor torque is less than a nominal torque threshold. The flowchart 3300 can be implemented by a control circuit, such as the control circuit 2500 (FIG. 7) in certain instances. In various instances, the flowchart 3300 can be implemented as a non-transitory computer readable medium storing computer readable instructions, and the non-transitory computer-readable medium can include any type of tangible machine-readable medium suitable for storing or transmitting electronic instructions or information in a form readable by a machine (e.g., a computer), which can implement the transitions between states in the flowchart 3300. In various instances, a memory for a robotic surgical system, such as the memory 2530 (FIG. 7) can store program instructions for performing the work calculation logic in the flowchart 3300, and a processor, such as the processor 2520 (FIG. 7) can be configured to execute the logic and steps of the flowchart 3300.

At the outset (or start) 3302 of the flowchart 3300, the robotic system can enter a grasping mode 3304, in which one or both of the jaws of the end effector are closed in teleoperation to grasp patient tissue. In the grasping mode 3304, the grasping work can initially be reset at a reset state 3306. In the reset state 3306, the grasping work calculation can also be reset (e.g. set to zero).

When the jaw(s) are closing, the flowchart 3300 transitions to a calculate state 3308, in which the grasping work is calculated. The grasping work calculation can ignore grasping work in the calculate state 3308 at an ignore sub-state 3310 when a Condition A 3312 is satisfied. The Condition A 3312 requires the closure motor torque for the respective time-step to be less than a nominal threshold torque stored in the memory. The grasping work calculation can accumulate grasping work in the calculate state 3308 at an accumulation sub-state 3309 when a Condition B 3313 is satisfied. The Condition B 3313 requires the closure motor torque for each time-step to be greater than or equal to the nominal threshold torque stored in the memory.

In instances in which multiple motors are utilized during the grasping mode 3304, a mean value from the torque sensors thereof can be compared to the nominal threshold torque for the Condition A 3312 and the Condition B 3313. In certain instances, an average torque can be calculated from the torque parameters from the torque sensors. In other instances, the calculate state 3308 can transition between the ignore sub-state 3310 and the accumulation sub-state 3309 in response to any motor torque meeting the condition triggering a transition.

If one or both jaws of the end effector begins to open, the flowchart 3300 transitions to the reset state 3306, in which the work calculation summation is reset. In other instances, the flowchart 3300 can transition to a pause state, in which the work calculation is held at its last and most-recent value for the stored position and orientation of the end effector in various instances, as further described herein. Determination of an opening jaw motion versus a closing jaw motion is further described herein.

The flowchart 3300 ensures that the work calculation accumulates while the jaws are closing and the closure motor torque is greater than or equal to the nominal threshold torque value. The nominal threshold torque can be determined during a manufacture of the end effector. In certain instances, the nominal torque threshold corresponds to the maximum recorded torque during a threshold grasping motion in which the first jaw and the second jaw are configured to move through the grasping motion without tissue being positioned therebetween. In various instances, the nominal torque threshold corresponds to a mean torque plus three times the standard deviation of the torque during an a threshold grasping motion in which the first jaw and the second jaw are configured to move through the grasping motion without tissue being positioned therebetween. The reader will appreciate that alternative standard deviation computations and statistical operations can be utilized to set the nominal torque threshold range based on torque values detected during the threshold grasping motion.

In various instances, only a staple cartridge is installed in the jaws during the threshold grasping motion. In various instances, upon connecting the surgical tool to a robotic surgical platform, the stored nominal threshold torque determined during manufacture can be communicated to the surgical robot and/or control circuit thereof.

The flowchart 3300 and work calculations thereof can continue throughout the grasping mode 3304 until an end (or termination) 3314 of the grasping mode 3304. In various instances, feedback can be transmitted to a GUI or alternative feedback device during the grasping mode 3304 as further described herein. Activation of a clamping actuator, such as a clamping pedal, for example, can terminate the grasping mode 3304 and initiate a clamping mode 3304 in various instances and, in other instances, a user input can terminate the grasping mode 3304 without initiating a clamping mode, as further described herein.

In various instances, the work-to-grasp calculation can depend on an internal state of the robotic tool. For example, the articulation angle of the robotic tool can impact the grasping work calculation. In such instances, the grasping work computation provided to a clinician may be skewed based on the internal state of the robotic tool. For example, at higher articulation angles, the variability in the grasping work computation can be distorted, which can bias a clinician's understanding of characteristics at the surgical site and give rise to misconceptions regarding tissue thickness, toughness, or other tissue characteristics, for example.

Figure 14:
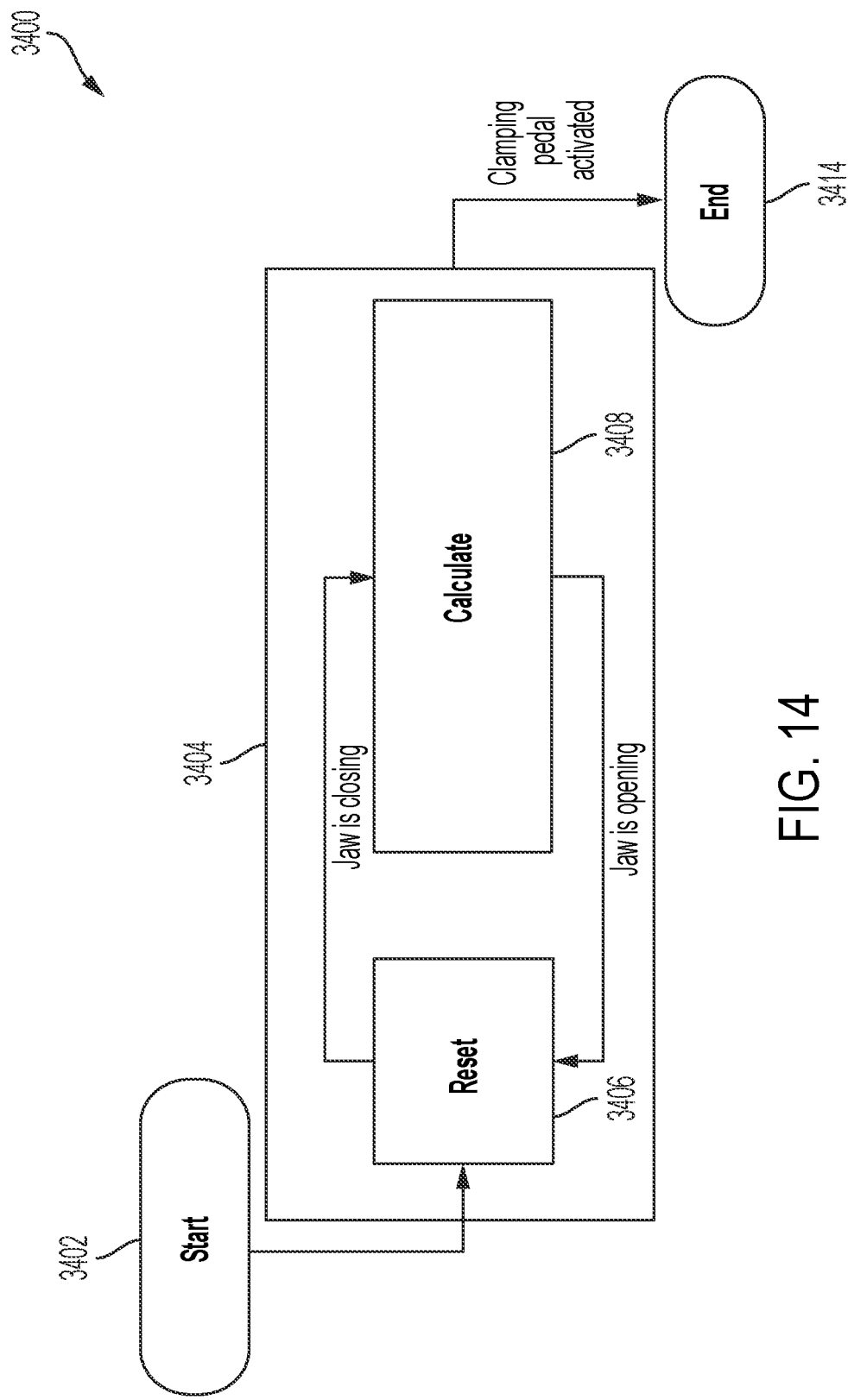
FIG. 14 is a logic diagram depicting a work calculation flowchart, in accordance with at least one aspect of the present disclosure.

Referring now to FIG. 14, a flowchart 3400 depicts work calculation logic for a robotic system and a robotic tool thereof, such as the robotic system 2100 (FIG. 1) and the robotic tool 2400 (FIG. 6), for example. The flowchart 3400 is similar in many aspects to the flowchart 3000; however, the work calculation includes an adjustment function for adjusting the grasping work calculation based on the articulation angle of the end effector. The flowchart 3400 can be implemented by a control circuit, such as the control circuit 2500 (FIG. 7) in certain instances. In various instances, the flowchart 3300 can be implemented as a non-transitory computer readable medium storing computer readable instructions, and the non-transitory computer-readable medium can include any type of tangible machine-readable medium suitable for storing or transmitting electronic instructions or information in a form readable by a machine (e.g., a computer), which can implement the transitions between states in the flowchart 3400. In various instances, a memory for a robotic surgical system, such as the memory 2530 (FIG. 7) can store program instructions for performing the work calculation logic in the flowchart 3400, and a processor, such as the processor 2520 (FIG. 7) can be configured to execute the logic and steps of the flowchart 3300.

At the outset (or start) 3402 of the flowchart 3400, the robotic system can enter a grasping mode 3404, in which one or both of the jaws of the end effector are closed in teleoperation to grasp patient tissue. In the grasping mode 3404, the grasping work can initially be reset at a reset state 3406. In the reset state 3406, the grasping work calculation can be reset (e.g. set to zero).

When the jaw(s) are closing, the flowchart 3400 transitions to a calculate state 3408, in which the grasping work is calculated. The grasping work can be calculated in the calculate state 3308 for each time-step or area under the curve of torque versus angle, where torque and angle are measured in real-time from the closure/grasping motor(s). In various instances, the grasping work can be calculated by taking the integral of torque detected by a load sensor coupled to each motor (e.g. the torque sensor 2508 in FIG. 7) over the angular displacement detected by a respective rotary output of the motor (e.g. the rotary encoder 2510 in FIG. 7). Moreover, at each time-step in the grasping work calculation, the grasping work can be multiplied by an articulation adjustment value based on the articulation angle of the end effector, which can adjust the work calculation to account for greater torques at greater articulation angles.

Figure 15:
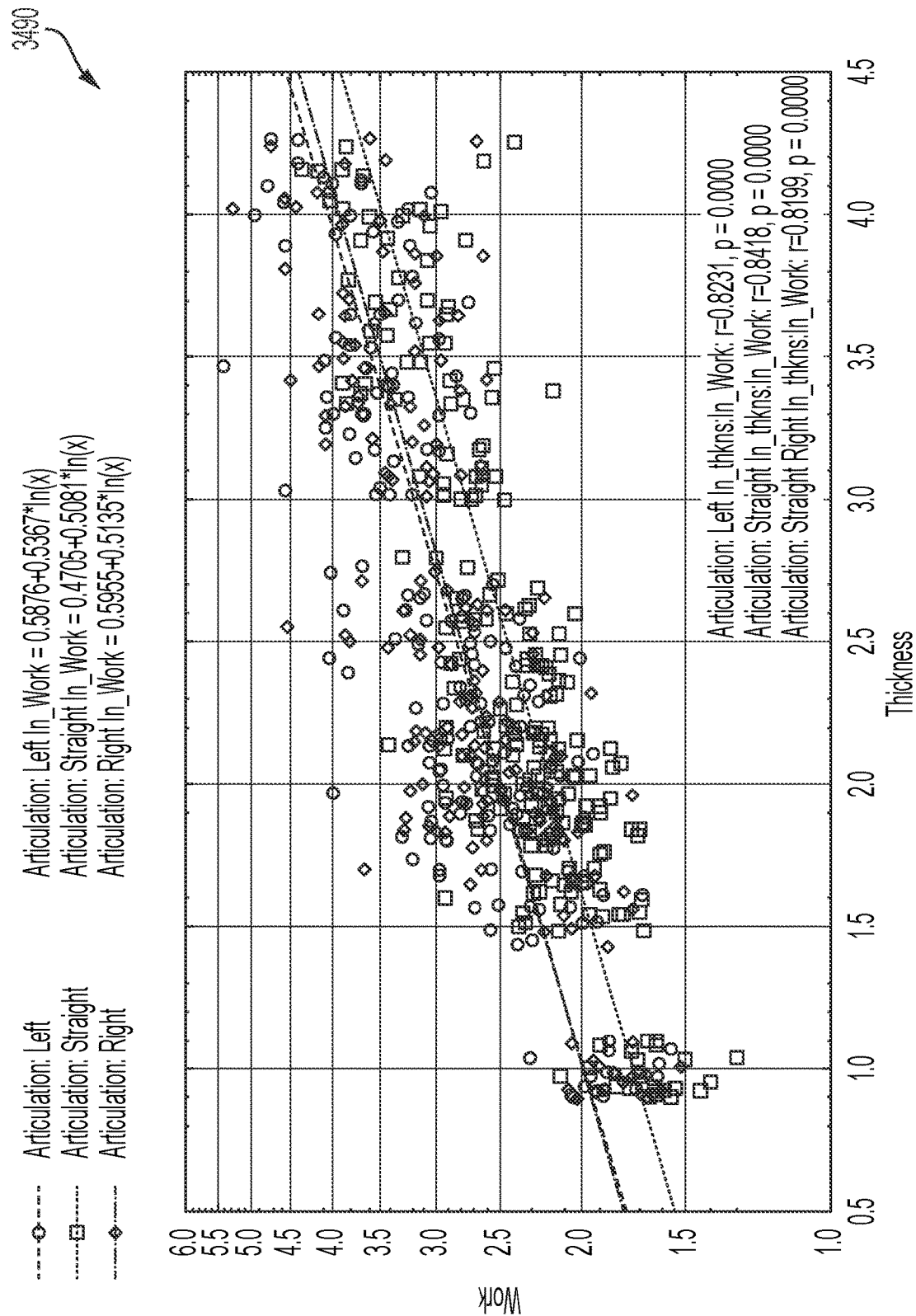
FIG. 15 is a scatterplot of grasping work against tissue thickness for different articulation angles and a non-articulated, straight end effector orientation, in accordance with at least one aspect of the present disclosure.

Referring now to FIG. 15, a scatterplot 3490 is shown in which grasping work calculations for different tissue thickness are characterized by different articulation angles. The scatterplot 3490 includes grasping work calculations when the surgical tool is articulated left 45 degrees, articulated right 45 degrees, and non-articulated/in a straight or linear orientation. In a straight orientation, the work calculations are generally lower than the work calculations in the articulated configurations at each tissue thickness. For example, the line-of-best-fit for the work performed when the surgical tool is non-articulated/straight is below the lines-of-best-fit for the work performed when the surgical tool is articulated. Moreover, the lines-of-best-fit for the 45-degree right and 45-degree left articulations are substantially similar and nearly collinear. In various instances, the lines-of-best-fit can be determined by a least squares method.

The articulation angle correction function is configured to normalize the work when the end effector is articulated to correct for the articulation angle. In such instances, the normalized work can be equivalent to the work performed on the tissue if the end effector were non-articulated/in a straight or linear orientation. In one aspect of the present disclosure, the articulation angle correction function is:

$$f(\text{articulation angle}) = m \times |\text{articulation angle}| + 1.$$

In instances in which the articulation angle is in degrees, the multiplier m can be between −0.002 and −0.004, for example, but can be any number in various instances. The value for the multiplier m is bound by the model generated by the scatterplot 3490 in which a particular surgical tool was tested on different tissue thicknesses at different articulation angles. The multiplier of −0.002 corresponds −0.1/45 and the multiplier −0.004 corresponds to −0.2/45; however, the reader will appreciate alternative multipliers, multiplier calculations, and/or articulation angle correction functions can be used. In certain instances, testing can include additional articulation angles between zero and the maximum articulation angle (e.g. 45 degrees in certain instances). Additionally or alternatively, multipliers for other articulation angles can be extrapolated from the scatterplot 3490 data. For example, a multiplier can be determined by testing the particular surgical tool on different tissue thicknesses. Upon applying the articulation angle adjustment formula to the grasping work at a particular time-step, the grasping work can be adjusted to account for the articulation angle.

Referring again to FIG. 14, if one or both jaws of the end effector begins to open, the flowchart 3400 transitions to the reset state 3406, in which the work calculation summation is reset. In other instances, the flowchart 3400 can transition to a pause state, in which the work calculation is held at its last and most-recent value for the stored position and orientation of the end effector in various instances, as further described herein. Determination of an opening jaw motion versus a closing jaw motion is further described herein.

The flowchart 3400 and work calculations thereof can continue throughout the grasping mode 3404 until an end (or termination) 3414 of the grasping mode 3404. In various instances, feedback can be transmitted to a GUI or alternative feedback device during the grasping mode 3404 as further described herein. Activation of a clamping actuator, such as a clamping pedal, for example, can terminate the grasping mode 3404 and initiate a clamping mode 3414 in various instances and, in other instances, a user input can terminate the grasping mode 3404 without initiating a clamping mode, as further described herein. The reader will further appreciate that the articulation angle adjustment function can be incorporated into the various calculation states further described herein.

The grasping work performed by a surgical end effector during a grasping motion can provide valuable and insightful information to a clinician regarding tissue properties. In certain instances, the grasping work can be adjusted and/or corrected for velocity of the clamping motion. For example, when tissue is squeezed more quickly, more force can be required to complete the closure motion and grasp the tissue. Therefore, the velocity of a grasping motion can result in a different amount of grasping work. Adjustments to the work calculation for velocity can be based on empirically-derived and/or stored tissue properties. However, in certain instances, tissue properties may not be known and/or may vary significantly over a range of tissue.

A characterization grasp can be utilized to determine certain tissue properties. In certain instances, a clinician can initiate a characterization grasp in which a prescribed angular displacement and/or torque from a robotic surgical tool are applied to tissue for one or more particular time periods and/or according to different grasping and/or ungrasping patterns. During the characterization grasp(s), the torque and angle over time can be detected and recorded. Properties of the tissue can be derived from this information. As tissue can vary from patient-to-patient, the characterization grasp can provide information specific to a particular tissue sample. In certain instances, damping properties of the tissue can be determined by the characterization grasp. Tissue properties determined during a characterization grasp can be used to adjust and/or correct the work-to-grasp calculation on subsequent grasping motions in certain instances. Such adjustments to the work-to-grasp calculation can be applied until a subsequent characterization grasp is applied.

Tissue is viscoelastic. During a characterization grasp, a surgical robot can grasp tissue at a controlled rate and the tissue's response can be utilized to calculate viscoelastic properties. Referring now to FIGS. 19A, 19B, 19C, and 20, the viscoelastic response of tissue can be modeled by a linear spring model 3650 (FIG. 19A) or 3670 (FIG. 19B), an adaptive quasi-linear viscoelastic (GLV) spring model 3680, or a rotary spring model 3660 (FIG. 20) to solve for the damping value n and the stiffness coefficient k.

For example, for the linear spring model 3650, force is dependent on the stiffness coefficient k, the displacement of the spring, the damping value n, and the derivative of the displacement with respect to time as follows:

$$F = k(d - do) + n\left(\frac{dd}{dt}\right).$$

For the rotary spring model 3660, torque is dependent on the stiffness coefficient k, the angular displacement of the spring, the damping value n, and the derivative of the angular displacement with respect to time as follows:

$$T = k(\theta - \theta o) + n\left(\frac{d\theta}{dt}\right).$$

The adaptive QLV spring model computations are further described in Nekouzadeh, Ali et al. "A simplified approach to quasi-linear viscoelastic modeling." *Journal of biomechanics* vol. 40,14 (2007): 3070-8. doi:10.1016/j.jbiomech.2007.03.019. The damping value n and the stiffness coefficient k can be back-calculated from these relationships/equations for a viscoelastic tissue sample during a characterization grasp based on the detected response for a known angular input over time. The phenomena of creep (deformation over time under a constant load) and relaxation (change in load over time under a constant displacement) correspond to the viscoelasticity of the tissue sample.

Figure 16:
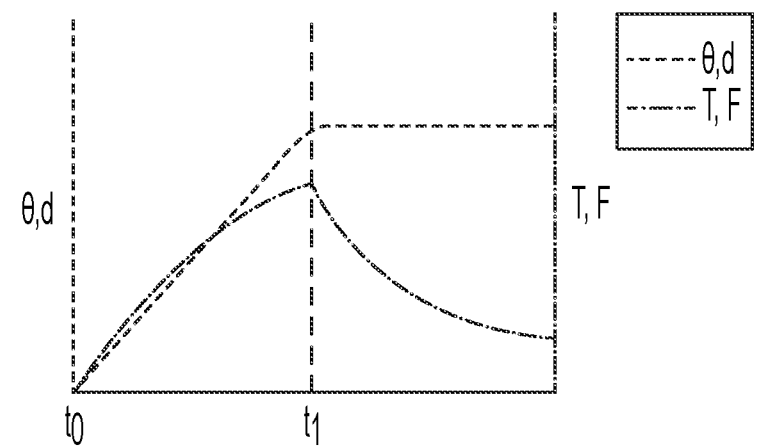
FIG. 16 is a graphical representation of displacement and force over time for a characterization grasp, in accordance with at least one aspect of the present disclosure.

Referring now to FIG. 16, output from a characterization grasp is shown in a graph 3600. The graph 3600 shows displacement and torque over time for a sample of tissue. In the characterization grasp of graph 3600, a displacement is implemented from time t0 to time t1, then the displacement motion is paused. The force/torque increases from time t0 to time t1 and the torque subsequently bleeds off after time t1 as the displacement remains constant. The bleed off of torque when the displacement is paused, i.e. after time t1, corresponds to a viscous property of the tissue.

Figure 17:
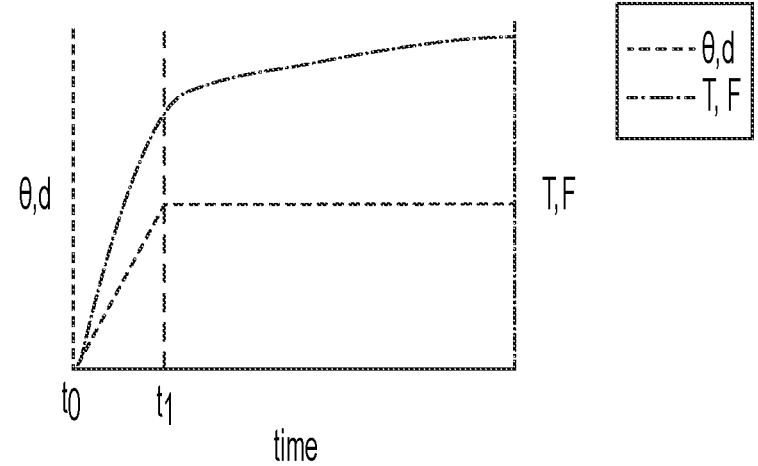
FIG. 17 is a graphical representation of displacement and force over time for another characterization grasp, in accordance with at least one aspect of the present disclosure.

Referring now to FIG. 17, output from another characterization grasp is shown in a graph 3610. The graph 3610 shows displacement and torque over time for a sample of tissue. In the characterization grasp of graph 3610, a displacement history is implemented such that a target load is reached at time t1 and then held constant thereafter. The change in displacement after time t1 is associated with the viscosity of the tissue.

Figure 18:
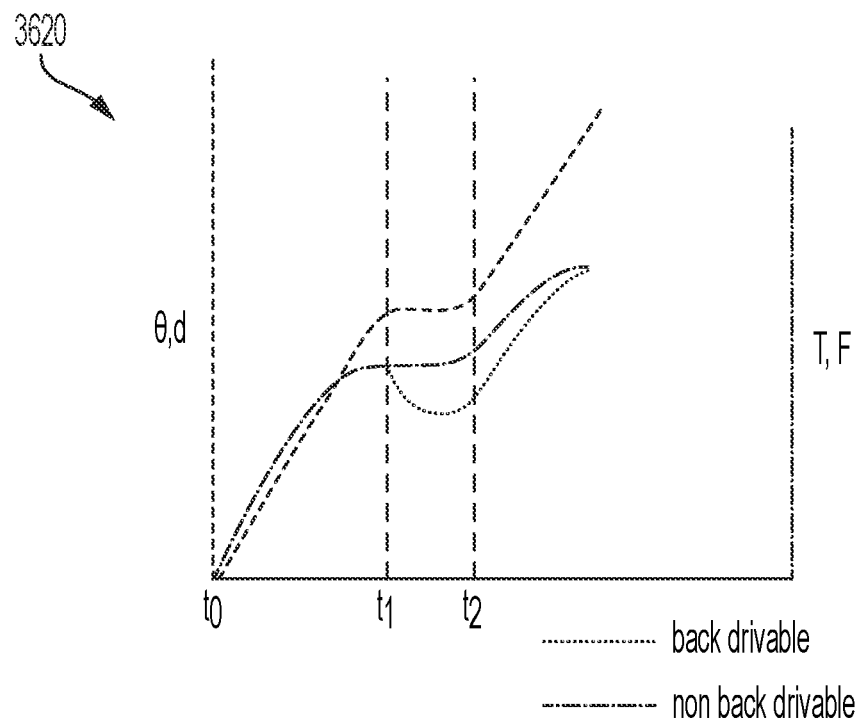
FIG. 18 is a graphical representation of displacement and force over time for another characterization grasp, in accordance with at least one aspect of the present disclosure.
Figures 19A, 19B:
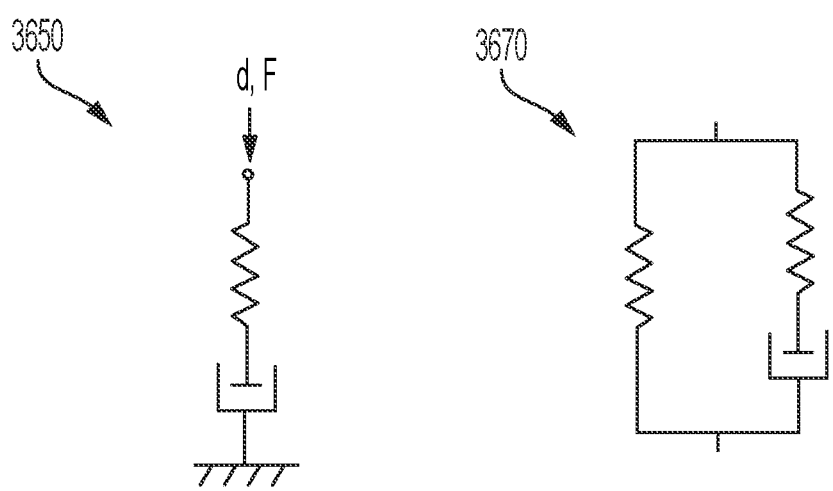
FIG. 19A is a linear spring model for viscoelastic tissue properties, in accordance with at least one aspect of the present disclosure.
FIG. 19B is a standard linear solid (SLS) spring model for viscoelastic tissue properties, in accordance with at least one aspect of the present disclosure.
Figure 19C:
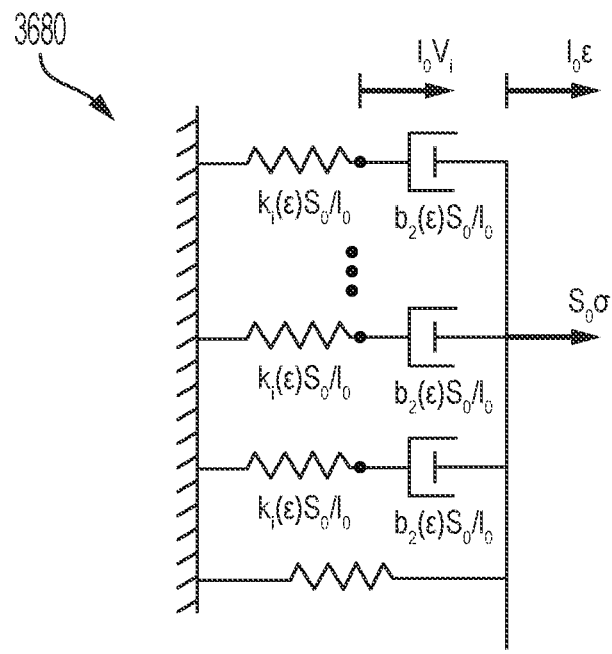
FIG. 19C is an adaptive quasi-linear viscoelastic (QLV) spring model for viscoelastic tissue properties, in accordance with at least one aspect of the present disclosure.
Figure 20:
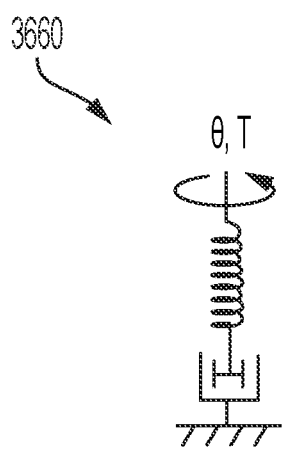
FIG. 20 is a rotary spring model for viscoelastic tissue properties, in accordance with at least one aspect of the present disclosure.

Referring now to FIG. 18, output from another characterization grasp is shown in a graph 3620. The graph 3620 shows displacement and torque over time for a sample of tissue. In the characterization grasp of graph 3620, a first displacement is implemented from time t0 to time t1, followed by a pause until time t2, and a second displacement is implemented after time t2. The force/torque also increases from time t0 to time t1 and after time t2. The difference in force/torque to move at time t1 can be compared to the force/torque to move at time t2 and the difference can be attributed to damping bleed off. The characterization grasp in graph 3620 can be helpful in characterizing tissue that cannot be back-driven. For example, non-back-drivable outputs are shown in the graph 3620.

In various instances, the output from the characterization grasp(s) can be compared to output plots of various tissue samples with specific tissue-properties and the closest match can be identified to approximate the tissue properties of the intraoperative tissue sample grasped with the characterization grasp(s).

Based on the tissue relaxation and/or tissue creep detected, recorded and graphed during the characterization grasp, damping properties of the tissue sample can be detected and the damping value n and/or the stiffness coefficient k can be calculated. In certain instances, one or more characterization grasps can be implemented by a surgical robot. Based on a surgical procedure and/or clinician's input, the first characterization grasp can be selected. A subsequent characterization grasp can be determined by the robotic control system based on the output of one or more proceeding characterization grasps in certain instances.

The robotic system is configured to calculate tissue properties during use and in real-time (or near-real time) based on output from the characterization grasps. Consequently, fewer assumptions are required of the clinician when identifying and/or correcting for tissue properties. For example, the values of the damping value n and the stiffness coefficient k can be back calculated during the characterization grasp(s) and used to adjust the work-to-grasp calculations on subsequent grasping motions based on intraoperative determinations of tissue properties.

A clinician can initiate a characterization grasp or grasping sequence in various ways. For example, the clinician can "double click" the grasp input control on the UID by initiating two quick and low magnitude pulses to the UID. The two pulses or grasps in quick succession can initiate a characterization grasp. In certain instances, a clutch can be engaged to switch the UID between operating controls. For example, the UID can be used to select a dedicated characterization grasping control on the GUI via a clutch. In certain instances, the characterization grasp(s) can be initiated from another user input control, such as a clamping actuator/pedal. For example, a brief pulse or input (in comparison to a click-and-hold input) on a clamping pedal can initiate a characterization grasping sequence in certain instances.

In certain instances, a sample of tissue can have unexpected tissue properties. For example, a clinician may select a particular tool, end effector, disposable loading unit, reload, and/or staple cartridge assembly based on the appearance of the tissue in combination with the clinician's experience. Upon grasping the tissue, a clinician may obtain output (e.g. grasping work calculations) related to the tissue difficulty. In certain instances, the output may indicate that the tissue is different than expected (e.g. thinner or thicker than expected). In such instances, the clinician may decide not to implement a clamping and/or firing stroke without further inspection and/or evaluation of the tissue. Before clamping and/or firing, the clinician may massage and/or further examine the patient's tissue. Additionally or alternatively, the clinician may exchange the surgical tool, end effector, disposable loading unit, reload, and/or replaceable staple cartridge assembly to better suit the tissue properties detected during the characterization grasping motion.

In certain instances, a grasping motion may only move through a portion of the grasping range as a result of torque limitations on the robotic tool. For example, the magnitude of grasping torque can be limited since high grasping torques can increase roll friction in certain instances. With limited torque, the grasping motion may stall at arbitrary angles, which can cut off the grasping work calculation. However, a clinician may still value information regarding the tissue properties, such as a tissue difficulty and/or grasping effort metric, for example, even in instances where torque limits stall the grasping motion prior to moving through the entire grasping range.

In various instances, a robotic surgical system can include statistics regarding grasping work for an entire tissue range at different grasping angles. Regardless of where a grasping motion is stalled, the grasping work can be extrapolated and compared, which can provide the surgeon with an indication of tissue properties.

Figure 21:
FIG. 21 is a 2-D lookup table for grasping metric normalization variables for various angle and work input values, according to at least one aspect of the present disclosure.

In one instance, a lookup table can include a grasp metric (or tissue difficulty metric) for each work and angle across different tissue samples encompassing the use range of the surgical tool. An exemplary 2D lookup table 3700 is shown in FIG. 21. To generate the 2D lookup table 3700, multiple representative surgical tools are clamped on randomized and measured tissue of different thicknesses encompassing the use range of the surgical tool. Torque and angle over time while grasping are recorded for each test such that the grasping work can be calculated through the full grasping range. Then, statistical properties for the grasping work are calculated for discrete increments of the grasping angle through the full grasping range. For example, the maximum work, minimum work, mean work, and standard deviations are calculated over the test clamping motions. These statistical properties can be saved in a memory (e.g. memory of the robotic surgical tool).

Figure 22:
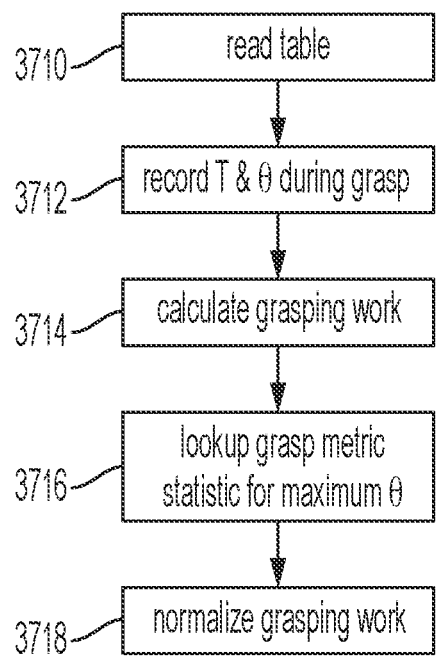
FIG. 22 is a flowchart for normalizing grasping work, in accordance with at least one aspect of the present disclosure.

Referring now to FIG. 22, a flowchart for utilizing grasp metric statistics to normalize grasping work is shown. At block 3710, the robotic surgical system can read the lookup table stored in the memory of the robotic surgical tool (e.g. lookup table 3700 in FIG. 21). During the surgical procedure, the robotic surgical system can record the torque and angular displacement over time during the grasping motion up to the maximum grasping angle at block 3712. Based on the detected torque and angular displacement, grasping work is calculated at block 3714. To normalize the grasping work calculation, grasp metric statistics for the maximum grasping angle can be found in the lookup table at block 3716. Then, the grasping work can be normalized at block 3718 based on this grasp metric statistics in the lookup table. The normalized grasping work can enable a clinician to compare grasping work independent of where grasping stalled to provide an improved indication of tissue properties to the clinician.

Figure 23:
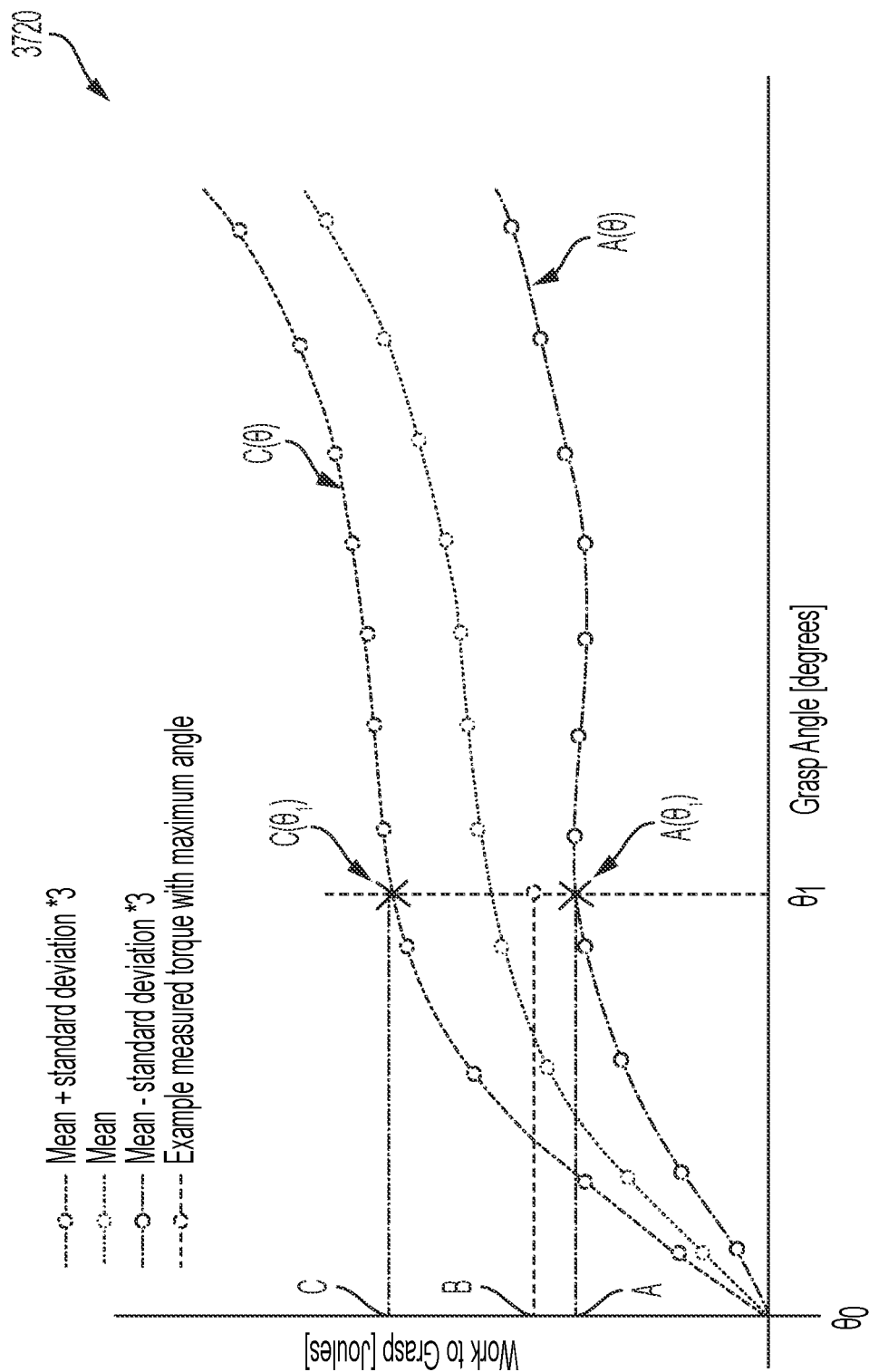
FIG. 23 is a graphical representation of grasping work over grasping angle for model tissue and further depicting a torque measurement at a maximum grasp angle for an example tissue sample, in accordance with at least one aspect of the present disclosure.

Referring now to FIG. 23, a graphical representation 3720 of example work-to-grasp calculations for example angular inputs is shown. The graphical statistical data is stored in a lookup table on the robotic tool, for example. During a grasping motion, the actual work-to-grasp is calculated from angle $\theta 0$ to angle $\theta 1$, which corresponds to the maximum grasping angle in a particular grasping motion. For example, the grasping motion may have stalled at angle $\theta 0$ due to resistance from the tissue. The work-to-grasp is calculated up to the angle $\theta 1$ and amounts to a work-to-grasp value of $B(\theta)$, which is less than the mean work-to-grasp at the angle $\theta 1$ and between the mean less three times the standard deviation of the work-to-grasp at the angle $\theta 1$.

In certain instances, the look-up table can include the angle $\theta 0$. Additionally, the look-up table can include the work-to-grasp value of "B" for the angle $\theta 1$ in certain instances. Based on the input angle and work-to-grasp, the grasping metric can be determined from the look-up table. In other instances, statistical values for the grasping work are interpolated. For example, the value of $B(\theta)$ can be entered into a grasping metric formula to calculate a grasping metric when the value of $B(\theta)$ is outside the range in the lookup table (e.g. greater than $C(\theta)$) for the maximum grasping angle. The grasping metric can be computed based on statistical values of grasping work for the angle $\theta 1$. The grasping metric is configured to compute an output within a predefined range (e.g. 0 to 100) regardless of where the maximum grasping angle occurred. In certain instances min-max scaling or min-max normalization can be applied to the grasping work. For example, the grasping metric formula can be:

$$\text{Grasp Metric} = 100 * \frac{B(\theta) - A(\theta)}{C(\theta) - A(\theta)}.$$

The value $A(\theta)$ corresponds to the minimum torque in a statistically meaningful range (e.g. mean less three times the standard deviation) and the value $C(\theta)$ corresponds to the maximum work-to-grasp in the statistically meaningful range (e.g. mean plus three times the standard deviation). The values $A(\theta)$ and $C(\theta)$ are stored in the lookup table. In other instances, the lookup table can include additional and/or alternative statistical metrics for calculating the grasp metric, such as the mean work-to-grasp value for each grasping angle.

Figure 24:
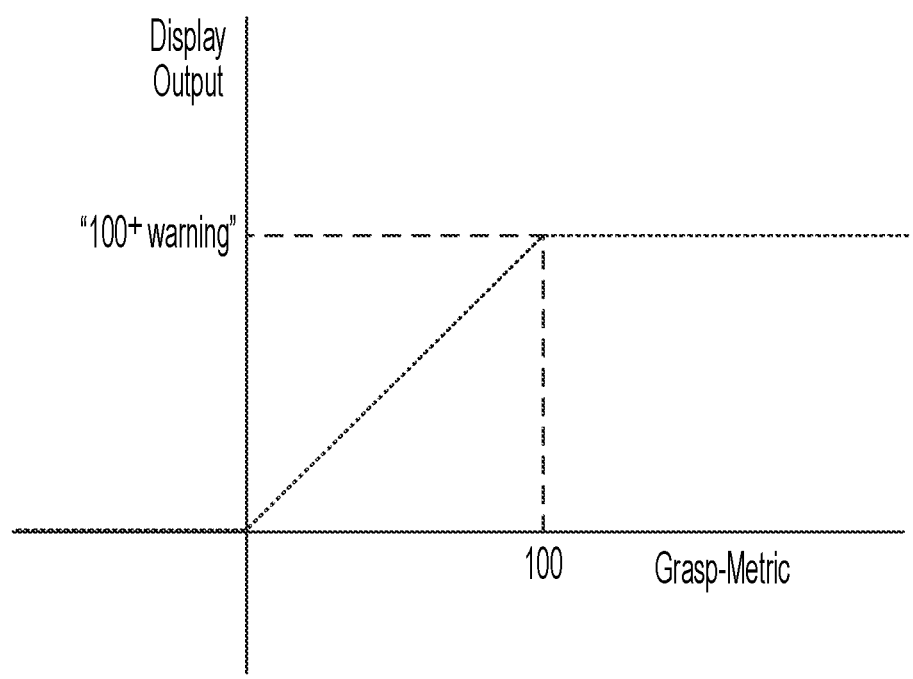
FIG. 24 is a graphical representation of a grasp metric and display output for indicating tissue difficulty to a clinician, in accordance with at least one aspect of the present disclosure.

Based on the computed grasp metric, the grasping work for a stalled grasping motion can be compared to other grasping metrics to provide tissue characterization insights to the clinician. Referring now to FIG. 24, a warning message can be issued to the clinician based on the grasping metric in certain instances. For example, wherein the grasping metric or normalized grasping work calculation is greater than a threshold value (e.g. greater than the maximum value of 100 in FIG. 24), a warning can be issued to the clinician. If the measured grasping work at a given angle $B(\theta)$ is greater than $C(\theta)$, for example, the metric will exceed 100. In such instances, the out-of-bound metric can be calculated as shown in FIGS. 23 and 24. Below the threshold value, the grasping metric value can be provided to the clinician. Feedback is provided the clinician via a communication device as further described herein. For example, a control circuit, upon completing a grasping metric calculation, can send a signal to a graphical user interface (e.g. GUI 2560 in FIG. 7). In other instances, the warning can be tactile (e.g. a vibration of the UID 2702) and/or auditory (e.g. a verbal warning and/or sequence of sounds from the robotic control console, for example).

EXAMPLES

Various aspects of the subject matter described herein are set out in the following numbered examples.

Example 1—A surgical system, comprising an end effector. The end effector comprises a first jaw and a second jaw, wherein at least one of the first jaw and the second jaw is configured to move through a grasping motion to grasp tissue therebetween. The surgical system further comprises a motor configured to drive the grasping motion, an encoder configured to detect rotary positions of the motor, and a load sensor configured to detect loads delivered by the motor. The surgical system further comprises a position sensor configured to detect three-dimensional positions of the end effector, and a control circuit comprising a processor and a memory communicatively coupled to the processor. The memory stores program instructions executable by the processor to receive a position parameter from the position sensor, a rotary parameter from the encoder, and a load parameter from the load sensor. The memory further stores program instructions executable by the processor to store the position parameter at the outset of the grasping motion in the memory, and calculate an amount of work performed by the motor during the grasping motion from the rotary parameter and the load parameter while the position sensor detects the position of the end effector remaining within a three-dimensional zone around the position parameter stored at the outset of the grasping motion. The memory further stores program instructions executable by the processor to transmit a work signal to a communication device indicative of the amount of work performed by the motor during the grasping motion, and reset the calculation of the amount of work performed by the motor during the grasping motion when the position sensor detects a displacement of the end effector out of the three-dimensional zone around the position parameter stored at the outset of the grasping motion.

Example 2—The surgical system of Example 1, wherein at least one of the first jaw and the second jaw is configured to move through an opening motion to release tissue grasped therebetween, and wherein the memory stores program instructions executable by the processor to pause the calculation of work performed by the motor during the opening motion.

Example 3—The surgical system of Example 2, when the encoder comprises a rotary encoder configured to detect the opening motion upon a reversal of the rotary direction of the motor.

Example 4—The surgical system of Example 1, 2, or 3, wherein the memory stores program instructions executable by the processor to terminate the calculation of work performed by the motor upon activation of a clamping actuator.

Example 5—The surgical system of Examples 1, 2, 3, or 4, wherein the calculation of the amount of work performed by the motor during the grasping motion comprising taking an integral of the load detected by the load sensor with respect to the position detected by the encoder while the position sensor detects the position of the end effector remaining with the three-dimensional zone around the position parameter stored at the outset of the grasping motion.

Example 6—The surgical system of Examples 1, 2, 3, 4, or 5, wherein the memory stores program instructions executable by the processor to transmit a reset signal to the communication device indicative of the position sensor detecting the position of the end effector outside the three-dimensional zone around the position parameter stored at the outset of the grasping motion.

Example 7—The surgical system of Examples 1, 2, 3, 4, 5, or 6, further comprising a robotic control unit comprising a robotic arm and the position sensor, wherein the position sensor comprises an arrangement of one-dimensional position sensors, wherein the robotic arm is configured to support the end effector, and wherein the position sensor is configured to utilize inverse kinematics to determine the position of the end effector.

Example 8—A surgical system, comprising an end effector comprising a first jaw and a second jaw, wherein at least one of the first jaw and the second jaw is configured to move through a grasping motion to grasp tissue therebetween. The surgical system further comprises a motor configured to drive the grasping motion, a rotary encoder configured to detect rotary positions of the motor, a torque sensor configured to detect torques delivered by the motor, and a control circuit comprising a processor and a memory communicatively coupled to the processor. The memory stores a nominal torque threshold and program instructions executable by the processor to receive rotary parameters from the rotary encoder and torque parameters from the torque sensor, accumulate an amount of work performed by the motor during the grasping motion from the rotary parameters and the torque parameters excluding work performed when the torque parameter is less than the nominal torque threshold, and transmit a work signal to a communication device indicative of the accumulated amount of work.

Example 9—The surgical system of Example 8, wherein the nominal torque threshold is determined during manufacture of the end effector.

Example 10—The surgical system of Examples 8 or 9, wherein the nominal torque threshold corresponds to the maximum recorded torque during a threshold grasping motion in which the first jaw and the second jaw are configured to move through the grasping motion without tissue being positioned therebetween.

Example 11—The surgical system of Examples 8 or 9, wherein the nominal torque threshold corresponds to a mean torque plus three times the standard deviation of the torque during an a threshold grasping motion in which the first jaw and the second jaw are configured to move through the grasping motion without tissue being positioned therebetween.

Example 12—The surgical system of Examples 8, 9, 10 or 11, wherein the end effector further comprises a replaceable staple cartridge installed therein during the threshold grasping motion.

Example 13—The surgical system of Examples 8, 9, 10, 11, or 12, wherein the motor comprises a first motor, wherein the rotary encoder comprises a first rotary encoder, and wherein the load sensor comprises a first torque sensor. The surgical system further comprises a second motor configured to drive the grasping motion, a second rotary encoder configured to detect rotary positions of the second motor, and a second torque sensor configured to detect torques delivered by the second motor. The memory stores program instructions executable by the processor to receive rotary parameters from the first rotary encoder and the second rotary encoder, receive torque parameters from the first torque sensor and the second torque sensor, accumulate the amount of work performed by the first motor and the second motor during the grasping motion from the rotary parameters and the torque parameters excluding work performed when the torque parameter from at least one of the first torque sensor and the second torque sensor is less than the nominal torque threshold, and transmit a work signal to a communication device indicative of the accumulated amount of work.

Example 14—A surgical system, comprising an end effector comprising a first jaw and a second jaw, wherein at least one of the first jaw and the second jaw is configured to move through a grasping motion to grasp tissue therebetween. The surgical system further comprises a first motor and a second motor configured to drive the grasping motion, a first rotary encoder configured to detect rotary positions of the first motor, and a second rotary encoder configured to detect rotary positions of the second motor. The surgical system further comprises a first torque sensor configured to detect torques delivered by the first motor, a second torque sensor configured to detect torques delivered by the second motor, and a control circuit comprising a processor and a memory communicatively coupled to the processor. The memory stores a nominal torque threshold and program instructions executable by the processor to receive rotary parameters from the first rotary encoder and the second rotary encoder, receive torque parameters from the first torque sensor and the second torque sensor, and calculate an average torque from the torque parameters. The memory further stores program instructions executable by the processor to accumulate an amount of work performed by the motor during the grasping motion from the rotary parameters and the torque parameters excluding work performed when the average torque is less than the nominal torque threshold, and transmit a work signal to a communication device indicative of the accumulated amount of work.

Example 15—A surgical system, comprising an end effector comprising a first jaw and a second jaw, wherein at least one of the first jaw and the second jaw is configured to move through a grasping motion to grasp tissue therebetween. The surgical system further comprises a motor configured to drive the grasping motion, a rotary encoder configured to detect rotary positions of the motor, and a torque sensor configured to detect torques delivered by the motor. The surgical system further comprises a control circuit comprising a processor and a memory communicatively coupled to the processor, wherein the memory stores a tissue metric lookup table in which a tissue metric output is associated with a maximum grasp angle. The memory further stores program instructions executable by the processor to receive rotary parameters from the rotary encoder and torque parameters from the torque sensor, calculate the work performed by the motor from the rotary parameters and the torque parameters, and identify the tissue metric output associated with the maximum grasp angle. The maximum grasp angle corresponds to the maximum rotary position of the motor during the grasping motion. The memory further stores program instructions executable by the processor to normalize the work performed by the motor based on the tissue metric output, and transmit a tissue metric signal to a communication device indicative of the work normalized with the tissue metric output.

Example 16—The surgical system of Example 15, wherein the tissue metric output associated with the maximum grasp angle is extrapolated from the work performed up to the maximum grasp angle and a standard deviation of the work at the maximum grasp angle.

Example 17—The surgical system of Example 15, wherein the tissue metric output associated with the maximum grasp angle is extrapolated to zero when the work performed by the motor is less than a threshold minimum work associated with the maximum grasp angle in the tissue metric lookup table.

Example 18—The surgical system of Example 15, wherein the tissue metric output associated with the maximum grasp angle is extrapolated to a maximum value when the work performed by the motor is greater than a threshold maximum work associated with the maximum grasp angle in the tissue metric lookup table.

Example 19—The surgical system of Example 18, wherein to normalize the work performed by the motor based on the tissue metric output comprises min-max scaling to bring the value into a range between zero and one.

Example 20—The surgical system of Examples 15, 16, 17, 18 or 19, wherein the memory further stores program instructions executable by the processor to transmit a warning to a communication device when the tissue metric output is extrapolated to a maximum value.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical system, comprising:
   an end effector comprising a first jaw and a second jaw, wherein at least one of the first jaw and the second jaw is configured to move through a grasping motion to grasp tissue therebetween;
   a motor configured to drive the grasping motion;
   a rotary encoder configured to detect rotary positions of the motor;
   a torque sensor configured to detect torques delivered by the motor; and
   a control circuit comprising a processor and a memory communicatively coupled to the processor, wherein the memory stores a nominal torque threshold and program instructions executable by the processor to:
      receive rotary parameters from the rotary encoder and torque parameters from the torque sensor;
      accumulate an amount of work performed by the motor during the grasping motion from the rotary parameters and the torque parameters excluding work performed when the torque parameter is less than the nominal torque threshold; and
      transmit a work signal to a communication device indicative of the accumulated amount of work.

2. The surgical system of claim 1, wherein the nominal torque threshold is determined during manufacture of the end effector.

3. The surgical system of claim 1, wherein the nominal torque threshold corresponds to the maximum recorded torque during a threshold grasping motion in which the first jaw and the second jaw are configured to move through the grasping motion without the tissue being positioned therebetween.

4. The surgical system of claim 1, wherein the nominal torque threshold corresponds to a mean torque plus three times a standard deviation of the torque during an a threshold grasping motion in which the first jaw and the second jaw are configured to move through the grasping motion without the tissue being positioned therebetween.

5. The surgical system of claim 4, wherein the end effector further comprises a replaceable staple cartridge installed therein during the threshold grasping motion.

6. The surgical system of claim 1, wherein the motor comprises a first motor, wherein the rotary encoder comprises a first rotary encoder, and wherein the torque sensor comprises a first torque sensor, and further comprising:
   a second motor configured to drive the grasping motion;
   a second rotary encoder configured to detect rotary positions of the second motor; and
   a second torque sensor configured to detect torques delivered by the second motor;
   wherein the memory stores program instructions executable by the processor to:
      receive rotary parameters from the first rotary encoder and the second rotary encoder;
      receive torque parameters from the first torque sensor and the second torque sensor;
      accumulate the amount of work performed by the first motor and the second motor during the grasping motion from the rotary parameters and the torque parameters excluding work performed when the torque parameter from at least one of the first torque sensor and the second torque sensor is less than the nominal torque threshold; and
      transmit a work signal to a communication device indicative of the accumulated amount of work.

7. A surgical system, comprising:
   an end effector comprising a first jaw and a second jaw, wherein at least one of the first jaw and the second jaw is configured to move through a grasping motion to grasp tissue therebetween;
   a first motor and a second motor configured to drive the grasping motion;
   a first rotary encoder configured to detect rotary positions of the first motor;
   a second rotary encoder configured to detect rotary positions of the second motor;
   a first torque sensor configured to detect torques delivered by the first motor;
   a second torque sensor configured to detect torques delivered by the second motor; and
   a control circuit comprising a processor and a memory communicatively coupled to the processor, wherein the memory stores a nominal torque threshold and program instructions executable by the processor to:
      receive rotary parameters from the first rotary encoder and the second rotary encoder;
      receive torque parameters from the first torque sensor and the second torque sensor;
      calculate an average torque from the torque parameters;
      accumulate an amount of work performed by the motor during the grasping motion from the rotary parameters and the torque parameters excluding work performed when the average torque is less than the nominal torque threshold; and
      transmit a work signal to a communication device indicative of the accumulated amount of work.

* * * * *